US012414823B2

(12) United States Patent
Ye et al.

(10) Patent No.: US 12,414,823 B2
(45) Date of Patent: Sep. 16, 2025

(54) ANATOMICAL FEATURE TRACKING

(71) Applicant: Auris Health, Inc., Santa Clara, CA (US)

(72) Inventors: Menglong Ye, Mountain View, CA (US); Yanwei Wang, Cambridge, MA (US); Elif Ayvali, Redwood City, CA (US); David Paul Noonan, San Francisco, CA (US)

(73) Assignee: Auris Health, Inc., Santa Clara, CA (US)

( * ) Notice: Subject to any disclaimer, the term of this patent is extended or adjusted under 35 U.S.C. 154(b) by 454 days.

(21) Appl. No.: 17/716,962

(22) Filed: Apr. 8, 2022

(65) Prior Publication Data

US 2022/0296312 A1 Sep. 22, 2022

Related U.S. Application Data

(63) Continuation of application No. 17/120,790, filed on Dec. 14, 2020, now Pat. No. 11,298,195.

(Continued)

(51) Int. Cl.
*A61B 34/20* (2016.01)
*A61B 1/00* (2006.01)
(Continued)

(52) U.S. Cl.
CPC ........ *A61B 34/20* (2016.02); *A61B 1/000094* (2022.02); *A61B 1/000096* (2022.02);
(Continued)

(58) Field of Classification Search
CPC .............. A61B 34/20; A61B 1/000094; A61B 1/000096; A61B 1/00042; A61B 1/042;
(Continued)

(56) References Cited

U.S. PATENT DOCUMENTS

| 631,949 | A | 8/1899 | Carlson |
| 639,109 | A | 12/1899 | Staeckig et al. |

(Continued)

FOREIGN PATENT DOCUMENTS

| CN | 1364275 A | 8/2002 |
| CN | 1511249 A | 7/2004 |

(Continued)

OTHER PUBLICATIONS

International Search Report and Written Opinion, dated Mar. 11, 2021, for PCT/IB2020/061908, 10-pages.

(Continued)

*Primary Examiner* — Sanjay Cattungal
(74) *Attorney, Agent, or Firm* — Paradice & Li LLP

(57) ABSTRACT

Anatomical feature tracking involves advancing a medical instrument to a treatment site of a patient, the medical instrument comprising an imaging device, generating a first image of at least a portion of the treatment site using the imaging device of the medical instrument when a distal end of the medical instrument is in a first position, generating a first silhouette of a first target anatomical feature represented in the first image, generating a second image of at least a portion of the treatment site using the imaging device of the medical instrument when the distal end of the medical instrument is in a second position, generating a second silhouette of a second target anatomical feature represented in the second image, and determining a target position at the treatment site based at least in part on the first silhouette and the second silhouette.

20 Claims, 12 Drawing Sheets

Related U.S. Application Data

(60) Provisional application No. 62/955,991, filed on Dec. 31, 2019.

(51) Int. Cl.
*A61B 1/04* (2006.01)
*A61B 34/10* (2016.01)
*A61B 34/37* (2016.01)
*G06N 3/04* (2023.01)
*G06N 3/08* (2023.01)
*A61B 34/30* (2016.01)

(52) U.S. Cl.
CPC .......... *A61B 1/00042* (2022.02); *A61B 1/042* (2013.01); *A61B 34/10* (2016.02); *A61B 34/37* (2016.02); *G06N 3/04* (2013.01); *G06N 3/08* (2013.01); *A61B 2034/107* (2016.02); *A61B 2034/2051* (2016.02); *A61B 2034/2074* (2016.02); *A61B 2034/301* (2016.02); *A61B 2560/0223* (2013.01)

(58) Field of Classification Search
CPC ... A61B 34/10; A61B 34/37; A61B 2034/107; A61B 2034/2051; A61B 2034/2074; A61B 2034/301; A61B 2560/0223; A61B 2017/00207; A61B 1/05; A61B 1/307; A61B 5/0084; A61B 5/061; A61B 2034/2048; A61B 2034/2061; A61B 2090/367; A61B 34/30; A61B 2034/302; A61B 34/71; A61B 34/74; A61B 90/361; A61B 2034/2065; A61B 34/25; A61B 90/37; G06N 3/04; G06N 3/08; G06N 3/045; G05B 2219/39271; G05B 2219/40494; B25J 9/1689; B25J 9/1697

See application file for complete search history.

(56) References Cited

U.S. PATENT DOCUMENTS

| | | |
|---|---|---|
| 646,291 A | 3/1900 | Krueger |
| 4,644,237 A | 2/1987 | Frushour et al. |
| 4,745,908 A | 5/1988 | Wardle |
| 4,748,969 A | 6/1988 | Wardle |
| 5,194,791 A | 3/1993 | Cull |
| 5,199,417 A | 4/1993 | Muller et al. |
| 5,251,611 A | 10/1993 | Zehel et al. |
| 5,273,025 A | 12/1993 | Sakiyama et al. |
| 5,280,781 A | 1/1994 | Oku |
| 5,408,263 A | 4/1995 | Kikuchi et al. |
| 5,526,812 A | 6/1996 | Dumoulin et al. |
| 5,550,953 A | 8/1996 | Seraji |
| 5,669,876 A | 9/1997 | Schechter et al. |
| 5,672,877 A | 9/1997 | Liebig et al. |
| 5,769,086 A | 6/1998 | Ritchart et al. |
| 5,831,614 A | 11/1998 | Tognazzini et al. |
| 5,876,325 A | 3/1999 | Mizuno et al. |
| 5,899,851 A | 5/1999 | Koninckx |
| 5,935,075 A | 8/1999 | Casscells et al. |
| 6,004,016 A | 12/1999 | Spector |
| 6,038,467 A | 3/2000 | Bliek et al. |
| 6,047,080 A | 4/2000 | Chen et al. |
| 6,059,718 A | 5/2000 | Taniguchi et al. |
| 6,063,095 A | 5/2000 | Wang et al. |
| 6,167,292 A | 12/2000 | Badano et al. |
| 6,198,974 B1 | 3/2001 | Webster, Jr. |
| 6,203,493 B1 | 3/2001 | Ben-Haim |
| 6,246,200 B1 | 6/2001 | Blumenkranz et al. |
| 6,246,784 B1 | 6/2001 | Summers et al. |
| 6,246,898 B1 | 6/2001 | Vesely et al. |
| 6,332,089 B1 | 12/2001 | Acker et al. |
| 6,425,865 B1 | 7/2002 | Salcudean et al. |
| 6,459,926 B1 | 10/2002 | Nowlin et al. |
| 6,466,198 B1 | 10/2002 | Feinstein |
| 6,490,467 B1 | 12/2002 | Bucholz et al. |
| 6,553,251 B1 | 4/2003 | Lähdesmäki |
| 6,665,554 B1 | 12/2003 | Charles et al. |
| 6,690,963 B2 | 2/2004 | Ben-Haim et al. |
| 6,690,964 B2 | 2/2004 | Bieger et al. |
| 6,755,797 B1 | 6/2004 | Stouffer |
| 6,812,842 B2 | 11/2004 | Dimmer |
| 6,837,846 B2 | 1/2005 | Jaffe et al. |
| 6,899,672 B2 | 5/2005 | Chin et al. |
| 6,926,709 B2 | 8/2005 | Bieger et al. |
| 7,130,700 B2 | 10/2006 | Gardeski et al. |
| 7,131,117 B2 | 10/2006 | Mills et al. |
| 7,180,976 B2 | 2/2007 | Wink et al. |
| 7,197,354 B2 | 3/2007 | Sobe |
| 7,206,627 B2 | 4/2007 | Abovitz et al. |
| 7,233,820 B2 | 6/2007 | Gilboa |
| 7,386,339 B2 | 6/2008 | Strommer et al. |
| 7,607,440 B2 | 10/2009 | Coste-Maniere et al. |
| 7,756,563 B2 | 7/2010 | Higgins et al. |
| 7,763,015 B2 | 7/2010 | Cooper et al. |
| 7,772,541 B2 | 8/2010 | Froggatt et al. |
| 7,850,642 B2 | 12/2010 | Moll et al. |
| 7,901,348 B2 | 3/2011 | Soper et al. |
| 7,963,288 B2 | 6/2011 | Rosenberg et al. |
| 8,021,325 B2 | 9/2011 | Zinger et al. |
| 8,021,326 B2 | 9/2011 | Moll et al. |
| 8,155,403 B2 | 4/2012 | Tschirren et al. |
| 8,190,238 B2 | 5/2012 | Moll et al. |
| 8,298,135 B2 | 10/2012 | Ito et al. |
| 8,317,746 B2 | 11/2012 | Sewell et al. |
| 8,335,557 B2 | 12/2012 | Maschke |
| 8,348,931 B2 | 1/2013 | Cooper et al. |
| 8,376,934 B2 | 2/2013 | Takahashi et al. |
| 8,394,054 B2 | 3/2013 | Wallace et al. |
| 8,396,595 B2 | 3/2013 | Dariush |
| 8,442,618 B2 | 5/2013 | Strommer et al. |
| 8,460,236 B2 | 6/2013 | Roelle et al. |
| 8,469,945 B2 | 6/2013 | Schena |
| 8,498,691 B2 | 7/2013 | Moll et al. |
| 8,506,555 B2 | 8/2013 | Morales |
| 8,554,368 B2 | 10/2013 | Fielding et al. |
| 8,652,030 B2 | 2/2014 | Matsuura et al. |
| 8,720,448 B2 | 5/2014 | Reis et al. |
| 8,738,181 B2 | 5/2014 | Greer et al. |
| 8,821,376 B2 | 9/2014 | Tolkowsky |
| 8,827,948 B2 | 9/2014 | Romo et al. |
| 8,858,424 B2 | 10/2014 | Hasegawa et al. |
| 8,894,610 B2 | 11/2014 | MacNamara et al. |
| 8,929,631 B2 | 1/2015 | Pfister et al. |
| 8,945,095 B2 | 2/2015 | Blumenkranz et al. |
| 9,014,851 B2 | 4/2015 | Wong et al. |
| 9,023,060 B2 | 5/2015 | Cooper et al. |
| 9,084,623 B2 | 7/2015 | Gomez et al. |
| 9,125,639 B2 | 9/2015 | Mathis et al. |
| 9,129,417 B2 | 9/2015 | Zheng et al. |
| 9,138,129 B2 | 9/2015 | Diolaiti |
| 9,173,713 B2 | 11/2015 | Hart et al. |
| 9,183,354 B2 | 11/2015 | Baker et al. |
| 9,186,046 B2 | 11/2015 | Ramamurthy et al. |
| 9,199,372 B2 | 12/2015 | Henderson et al. |
| 9,226,796 B2 | 1/2016 | Bowling et al. |
| 9,256,940 B2 | 2/2016 | Carelsen et al. |
| 9,259,274 B2 | 2/2016 | Prisco |
| 9,272,416 B2 | 3/2016 | Hourtash et al. |
| 9,289,578 B2 | 3/2016 | Walker et al. |
| 9,302,702 B1 | 4/2016 | Schepmann et al. |
| 9,314,306 B2 | 4/2016 | Yu |
| 9,345,456 B2 | 5/2016 | Tsonton et al. |
| 9,358,682 B2 | 6/2016 | Morales |
| 9,452,276 B2 | 9/2016 | Duindam et al. |
| 9,459,087 B2 | 10/2016 | Dunbar et al. |
| 9,504,604 B2 | 11/2016 | Alvarez |
| 9,522,034 B2 | 12/2016 | Johnson et al. |
| 9,547,908 B1 | 1/2017 | Kim et al. |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,595 B2 | 4/2017 | Walker et al. |

(56) References Cited

U.S. PATENT DOCUMENTS

| | | |
|---|---|---|
| 9,629,682 B2 | 4/2017 | Wallace et al. |
| 9,636,184 B2 | 5/2017 | Lee et al. |
| 9,668,768 B2 | 6/2017 | Piron et al. |
| 9,675,422 B2 | 6/2017 | Hourtash et al. |
| 9,710,921 B2 | 7/2017 | Wong et al. |
| 9,713,509 B2 | 7/2017 | Schuh et al. |
| 9,717,563 B2 | 8/2017 | Tognaccini et al. |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,782,229 B2 | 10/2017 | Crawford et al. |
| 9,788,910 B2 | 10/2017 | Schuh |
| 9,789,608 B2 | 10/2017 | Itkowitz et al. |
| 9,839,481 B2 | 12/2017 | Blumenkranz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,123,755 B2 | 11/2018 | Walker et al. |
| 10,130,345 B2 | 11/2018 | Wong et al. |
| 10,130,427 B2 | 11/2018 | Tanner et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,251,713 B2 | 4/2019 | Morales et al. |
| 10,271,915 B2 | 4/2019 | Diolaiti et al. |
| 10,278,778 B2 | 5/2019 | State et al. |
| 10,285,574 B2 | 5/2019 | Andey et al. |
| 10,299,870 B2 | 5/2019 | Connolly et al. |
| 10,314,463 B2 | 6/2019 | Agrawal et al. |
| 10,342,410 B2 | 7/2019 | Schwartz et al. |
| 10,383,765 B2 | 8/2019 | Alvarez et al. |
| 10,398,518 B2 | 9/2019 | Yu et al. |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,454,347 B2 | 10/2019 | Covington et al. |
| 10,464,209 B2 | 11/2019 | Ho et al. |
| 10,470,830 B2 | 11/2019 | Hill et al. |
| 10,482,599 B2 | 11/2019 | Mintz et al. |
| 10,489,913 B2 | 11/2019 | Shi |
| 10,492,741 B2 | 12/2019 | Walker et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan et al. |
| 10,531,864 B2 | 1/2020 | Wong et al. |
| 10,539,478 B2 | 1/2020 | Lin et al. |
| 10,543,048 B2 | 1/2020 | Noonan |
| 10,555,775 B2 | 2/2020 | Hoffman et al. |
| 10,555,778 B2 | 2/2020 | Ummalaneni |
| 10,575,906 B2 | 3/2020 | Wu |
| 10,582,907 B2 | 3/2020 | Chen et al. |
| 10,583,271 B2 | 3/2020 | Bogusky |
| 10,631,949 B2 | 4/2020 | Schuh et al. |
| 10,639,109 B2 | 5/2020 | Bovay et al. |
| 10,646,291 B2 | 5/2020 | Turner |
| 10,779,711 B2 | 9/2020 | Schena |
| 10,918,307 B2 | 2/2021 | Olson et al. |
| 11,135,023 B2 | 10/2021 | Larkin et al. |
| 11,172,895 B2 | 11/2021 | Dickhans et al. |
| 11,311,343 B2 | 4/2022 | Lwin et al. |
| 11,737,663 B2 | 8/2023 | Ayvali et al. |
| 2001/0000040 A1 | 3/2001 | Adams et al. |
| 2001/0021843 A1 | 9/2001 | Bosselmann et al. |
| 2001/0039421 A1 | 11/2001 | Heilbrun et al. |
| 2002/0035330 A1 | 3/2002 | Cline et al. |
| 2002/0065455 A1 | 5/2002 | Ben-Haim et al. |
| 2002/0077533 A1 | 6/2002 | Bieger et al. |
| 2002/0082612 A1 | 6/2002 | Moll et al. |
| 2002/0120188 A1 | 8/2002 | Brock et al. |
| 2002/0128535 A1 | 9/2002 | Kikuchi et al. |
| 2002/0161280 A1 | 10/2002 | Chatenever et al. |
| 2002/0173878 A1 | 11/2002 | Watanabe et al. |
| 2003/0045778 A1 | 3/2003 | Ohline et al. |
| 2003/0105603 A1 | 6/2003 | Hardesty |
| 2003/0125622 A1 | 7/2003 | Schweikard et al. |
| 2003/0158628 A1 | 8/2003 | Matsuoka et al. |
| 2003/0181809 A1 | 9/2003 | Hall et al. |
| 2003/0182091 A1 | 9/2003 | Kukuk |
| 2003/0195664 A1 | 10/2003 | Nowlin et al. |
| 2003/0199765 A1* | 10/2003 | Stetten ............... A61B 8/00 600/439 |
| 2003/0209096 A1 | 11/2003 | Pandey et al. |
| 2004/0047044 A1 | 3/2004 | Dalton |
| 2004/0072066 A1 | 4/2004 | Cho et al. |
| 2004/0176751 A1 | 9/2004 | Weitzner et al. |
| 2004/0186349 A1 | 9/2004 | Ewers et al. |
| 2004/0249267 A1 | 12/2004 | Gilboa |
| 2004/0257021 A1 | 12/2004 | Chang et al. |
| 2004/0263535 A1 | 12/2004 | Birkenbach et al. |
| 2004/0267477 A1 | 12/2004 | Scott et al. |
| 2005/0027397 A1 | 2/2005 | Niemeyer |
| 2005/0043718 A1 | 2/2005 | Madhani et al. |
| 2005/0060006 A1 | 3/2005 | Pflueger et al. |
| 2005/0065400 A1 | 3/2005 | Banik et al. |
| 2005/0080333 A1* | 4/2005 | Piron ............... G01S 7/52049 600/417 |
| 2005/0085714 A1 | 4/2005 | Foley et al. |
| 2005/0107679 A1 | 5/2005 | Geiger et al. |
| 2005/0107917 A1 | 5/2005 | Smith et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0193451 A1 | 9/2005 | Quistgaard et al. |
| 2005/0203382 A1 | 9/2005 | Govari et al. |
| 2005/0222554 A1 | 10/2005 | Wallace et al. |
| 2005/0234293 A1 | 10/2005 | Yamamoto et al. |
| 2005/0256398 A1 | 11/2005 | Hastings et al. |
| 2005/0261551 A1 | 11/2005 | Couvillon, Jr. et al. |
| 2005/0272975 A1 | 12/2005 | McWeeney et al. |
| 2006/0004286 A1 | 1/2006 | Chang et al. |
| 2006/0015096 A1 | 1/2006 | Hauck et al. |
| 2006/0025668 A1 | 2/2006 | Peterson et al. |
| 2006/0041293 A1 | 2/2006 | Mehdizadeh et al. |
| 2006/0058617 A1 | 3/2006 | Sano et al. |
| 2006/0058643 A1 | 3/2006 | Florent et al. |
| 2006/0079745 A1 | 4/2006 | Viswanathan |
| 2006/0084860 A1 | 4/2006 | Geiger et al. |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0161136 A1 | 7/2006 | Anderson et al. |
| 2006/0167440 A1 | 7/2006 | Cooper et al. |
| 2006/0173290 A1 | 8/2006 | Lavallee et al. |
| 2006/0178556 A1 | 8/2006 | Hasser et al. |
| 2006/0184016 A1 | 8/2006 | Glossop |
| 2006/0200026 A1 | 9/2006 | Wallace et al. |

(56) References Cited

U.S. PATENT DOCUMENTS

| | | |
|---|---|---|
| 2006/0200049 A1 | 9/2006 | Leo et al. |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2006/0287769 A1 | 12/2006 | Yanagita et al. |
| 2007/0013336 A1 | 1/2007 | Nowlin et al. |
| 2007/0032826 A1 | 2/2007 | Schwartz |
| 2007/0043455 A1 | 2/2007 | Viswanathan et al. |
| 2007/0055128 A1 | 3/2007 | Glossop |
| 2007/0055144 A1 | 3/2007 | Neustadter et al. |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0142971 A1 | 6/2007 | Schena et al. |
| 2007/0150155 A1 | 6/2007 | Kawai et al. |
| 2007/0156019 A1 | 7/2007 | Larkin et al. |
| 2007/0161857 A1 | 7/2007 | Durant et al. |
| 2007/0167743 A1 | 7/2007 | Honda et al. |
| 2007/0167801 A1 | 7/2007 | Webler et al. |
| 2007/0173694 A1 | 7/2007 | Tsuji et al. |
| 2007/0208252 A1 | 9/2007 | Makower |
| 2007/0232856 A1 | 10/2007 | Ueno et al. |
| 2007/0249911 A1 | 10/2007 | Simon |
| 2007/0253599 A1 | 11/2007 | White et al. |
| 2007/0269001 A1 | 11/2007 | Maschke |
| 2007/0287992 A1 | 12/2007 | Diolaiti et al. |
| 2007/0293721 A1 | 12/2007 | Gilboa |
| 2007/0299353 A1 | 12/2007 | Harlev et al. |
| 2008/0027313 A1 | 1/2008 | Shachar |
| 2008/0046122 A1 | 2/2008 | Manzo et al. |
| 2008/0071140 A1 | 3/2008 | Gattani et al. |
| 2008/0079421 A1 | 4/2008 | Jensen |
| 2008/0081982 A1* | 4/2008 | Simon .................... A61B 90/06 600/407 |
| 2008/0103389 A1 | 5/2008 | Begelman et al. |
| 2008/0108870 A1 | 5/2008 | Wiita et al. |
| 2008/0118118 A1 | 5/2008 | Berger |
| 2008/0118135 A1 | 5/2008 | Averbuch et al. |
| 2008/0123921 A1 | 5/2008 | Gielen et al. |
| 2008/0140087 A1 | 6/2008 | Barbagli |
| 2008/0147089 A1 | 6/2008 | Loh et al. |
| 2008/0159653 A1 | 7/2008 | Dunki-Jacobs et al. |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218588 A1* | 9/2008 | Stetten .................... A61B 8/462 348/46 |
| 2008/0218743 A1* | 9/2008 | Stetten .................... A61B 90/36 356/73 |
| 2008/0218770 A1 | 9/2008 | Moll et al. |
| 2008/0231221 A1 | 9/2008 | Ogawa |
| 2008/0243142 A1 | 10/2008 | Gildenberg |
| 2008/0249640 A1 | 10/2008 | Vittor et al. |
| 2008/0255505 A1 | 10/2008 | Carlson et al. |
| 2008/0262297 A1 | 10/2008 | Gilboa et al. |
| 2008/0275349 A1 | 11/2008 | Halperin et al. |
| 2008/0287963 A1 | 11/2008 | Rogers et al. |
| 2008/0300478 A1* | 12/2008 | Zuhars .................... A61B 34/20 600/407 |
| 2008/0306490 A1 | 12/2008 | Lakin et al. |
| 2008/0312501 A1 | 12/2008 | Hasegawa et al. |
| 2008/0312771 A1 | 12/2008 | Sugiura |
| 2009/0005768 A1 | 1/2009 | Sharareh et al. |
| 2009/0030307 A1 | 1/2009 | Govari et al. |
| 2009/0048611 A1 | 2/2009 | Funda et al. |
| 2009/0054729 A1 | 2/2009 | Mori et al. |
| 2009/0062611 A1 | 3/2009 | Toyama |
| 2009/0062813 A1 | 3/2009 | Prisco et al. |
| 2009/0076476 A1 | 3/2009 | Barbagli et al. |
| 2009/0076534 A1 | 3/2009 | Shelton et al. |
| 2009/0149867 A1 | 6/2009 | Glozman et al. |
| 2009/0184825 A1 | 7/2009 | Anderson |
| 2009/0198298 A1 | 8/2009 | Kaiser et al. |
| 2009/0227861 A1 | 9/2009 | Ganatra et al. |
| 2009/0228020 A1 | 9/2009 | Wallace et al. |
| 2009/0245600 A1 | 10/2009 | Hoffman et al. |
| 2009/0248036 A1 | 10/2009 | Hoffman et al. |
| 2009/0256905 A1 | 10/2009 | Tashiro |
| 2009/0259099 A1 | 10/2009 | Zhou et al. |
| 2009/0259230 A1 | 10/2009 | Khadem et al. |
| 2009/0262109 A1 | 10/2009 | Markowitz et al. |
| 2009/0287354 A1 | 11/2009 | Choi |
| 2009/0292166 A1 | 11/2009 | Ito et al. |
| 2009/0295797 A1 | 12/2009 | Sakaguchi |
| 2009/0324161 A1 | 12/2009 | Prisco |
| 2009/0326318 A1 | 12/2009 | Tognaccini et al. |
| 2010/0008555 A1 | 1/2010 | Trumer et al. |
| 2010/0030061 A1 | 2/2010 | Canfield et al. |
| 2010/0030115 A1 | 2/2010 | Fujimoto et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0069920 A1 | 3/2010 | Naylor et al. |
| 2010/0076263 A1 | 3/2010 | Tanaka et al. |
| 2010/0082041 A1 | 4/2010 | Prisco |
| 2010/0121138 A1 | 5/2010 | Goldenberg et al. |
| 2010/0121139 A1 | 5/2010 | OuYang et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0168918 A1 | 7/2010 | Zhao et al. |
| 2010/0198170 A1 | 8/2010 | Umeda et al. |
| 2010/0204713 A1 | 8/2010 | Morales |
| 2010/0225209 A1 | 9/2010 | Goldberg et al. |
| 2010/0228266 A1 | 9/2010 | Hourtash |
| 2010/0234856 A1 | 9/2010 | Stoianovici et al. |
| 2010/0234857 A1 | 9/2010 | Itkowitz et al. |
| 2010/0240989 A1 | 9/2010 | Stoianovici et al. |
| 2010/0256812 A1 | 10/2010 | Tsusaka et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0009880 A1 | 1/2011 | Prisco et al. |
| 2011/0015484 A1 | 1/2011 | Alvarez et al. |
| 2011/0021926 A1 | 1/2011 | Spencer et al. |
| 2011/0054303 A1 | 3/2011 | Barrick et al. |
| 2011/0082366 A1 | 4/2011 | Scully et al. |
| 2011/0082462 A1 | 4/2011 | Suarez et al. |
| 2011/0092808 A1 | 4/2011 | Shachar et al. |
| 2011/0137122 A1 | 6/2011 | Kawai |
| 2011/0153252 A1 | 6/2011 | Govari et al. |
| 2011/0160570 A1 | 6/2011 | Kariv et al. |
| 2011/0184238 A1 | 7/2011 | Higgins et al. |
| 2011/0196199 A1 | 8/2011 | Donhowe et al. |
| 2011/0218676 A1 | 9/2011 | Okazaki |
| 2011/0234780 A1 | 9/2011 | Ito et al. |
| 2011/0238082 A1 | 9/2011 | Wenderow et al. |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0257480 A1 | 10/2011 | Takahashi et al. |
| 2011/0258842 A1 | 10/2011 | Dukesherer et al. |
| 2011/0270084 A1 | 11/2011 | Choi et al. |
| 2011/0276179 A1 | 11/2011 | Banks et al. |
| 2011/0277775 A1 | 11/2011 | Holop et al. |
| 2011/0319910 A1 | 12/2011 | Roelle et al. |
| 2012/0000427 A1 | 1/2012 | Nilsson |
| 2012/0046521 A1 | 2/2012 | Hunter et al. |
| 2012/0046522 A1 | 2/2012 | Naito |
| 2012/0056986 A1 | 3/2012 | Popovic |
| 2012/0059249 A1 | 3/2012 | Verard et al. |
| 2012/0062714 A1 | 3/2012 | Liu et al. |
| 2012/0065481 A1 | 3/2012 | Hunter et al. |
| 2012/0069167 A1 | 3/2012 | Liu et al. |
| 2012/0071752 A1 | 3/2012 | Sewell et al. |
| 2012/0071782 A1 | 3/2012 | Patil et al. |
| 2012/0071822 A1 | 3/2012 | Romo et al. |

(56) References Cited

U.S. PATENT DOCUMENTS

| | | |
|---|---|---|
| 2012/0071894 A1 | 3/2012 | Tanner et al. |
| 2012/0082351 A1 | 4/2012 | Higgins et al. |
| 2012/0120305 A1 | 5/2012 | Takahashi |
| 2012/0123441 A1 | 5/2012 | Au et al. |
| 2012/0130217 A1 | 5/2012 | Kauphusman et al. |
| 2012/0136372 A1 | 5/2012 | Girbau et al. |
| 2012/0165656 A1 | 6/2012 | Montag et al. |
| 2012/0191079 A1 | 7/2012 | Moll et al. |
| 2012/0209069 A1 | 8/2012 | Popovic et al. |
| 2012/0209293 A1 | 8/2012 | Carlson et al. |
| 2012/0215094 A1 | 8/2012 | Rahimian et al. |
| 2012/0219185 A1 | 8/2012 | Hu et al. |
| 2012/0221007 A1 | 8/2012 | Batten et al. |
| 2012/0239060 A1 | 9/2012 | Orban, III |
| 2012/0253276 A1 | 10/2012 | Govari et al. |
| 2012/0283745 A1 | 11/2012 | Goldberg et al. |
| 2012/0283747 A1 | 11/2012 | Popovic |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2012/0328077 A1 | 12/2012 | Bouvier |
| 2013/0018306 A1 | 1/2013 | Ludwin |
| 2013/0060146 A1 | 3/2013 | Yang et al. |
| 2013/0085330 A1 | 4/2013 | Ramamurthy et al. |
| 2013/0090530 A1 | 4/2013 | Ramamurthy et al. |
| 2013/0102846 A1 | 4/2013 | Sjostrom et al. |
| 2013/0123580 A1 | 5/2013 | Peters et al. |
| 2013/0131503 A1 | 5/2013 | Schneider et al. |
| 2013/0144116 A1 | 6/2013 | Cooper et al. |
| 2013/0165854 A1 | 6/2013 | Sandhu et al. |
| 2013/0165945 A9 | 6/2013 | Roelle et al. |
| 2013/0204124 A1 | 8/2013 | Duindam et al. |
| 2013/0209208 A1 | 8/2013 | Bailey et al. |
| 2013/0218005 A1 | 8/2013 | Desai et al. |
| 2013/0225942 A1 | 8/2013 | Holsing et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0274783 A1 | 10/2013 | Wynberg |
| 2013/0303891 A1 | 11/2013 | Chopra et al. |
| 2013/0303892 A1 | 11/2013 | Zhao et al. |
| 2013/0325030 A1 | 12/2013 | Hourtash et al. |
| 2013/0345718 A1 | 12/2013 | Crawford et al. |
| 2014/0001235 A1 | 1/2014 | Shelton, IV |
| 2014/0051049 A1 | 2/2014 | Jarc et al. |
| 2014/0051985 A1 | 2/2014 | Fan et al. |
| 2014/0058406 A1 | 2/2014 | Tsekos |
| 2014/0107390 A1 | 4/2014 | Brown et al. |
| 2014/0114180 A1 | 4/2014 | Jain et al. |
| 2014/0135985 A1 | 5/2014 | Coste-Maniere et al. |
| 2014/0142591 A1 | 5/2014 | Alvarez et al. |
| 2014/0148808 A1 | 5/2014 | Inkpen et al. |
| 2014/0163664 A1 | 6/2014 | Goldsmith |
| 2014/0180063 A1 | 6/2014 | Zhao et al. |
| 2014/0222207 A1 | 8/2014 | Bowling et al. |
| 2014/0235943 A1 | 8/2014 | Paris et al. |
| 2014/0243801 A1 | 8/2014 | Fanelli et al. |
| 2014/0243849 A1 | 8/2014 | Saglam et al. |
| 2014/0257333 A1 | 9/2014 | Blumenkranz |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276937 A1 | 9/2014 | Wong et al. |
| 2014/0277333 A1 | 9/2014 | Lewis et al. |
| 2014/0296655 A1 | 10/2014 | Akhbardeh et al. |
| 2014/0296657 A1 | 10/2014 | Izmirli et al. |
| 2014/0296870 A1 | 10/2014 | Stern et al. |
| 2014/0309527 A1 | 10/2014 | Namati et al. |
| 2014/0309625 A1 | 10/2014 | Okamoto et al. |
| 2014/0316420 A1 | 10/2014 | Ballard et al. |
| 2014/0343416 A1 | 11/2014 | Panescu et al. |
| 2014/0343569 A1 | 11/2014 | Turner |
| 2014/0350391 A1 | 11/2014 | Prisco et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2015/0025549 A1 | 1/2015 | Kilroy et al. |
| 2015/0045675 A1 | 2/2015 | Chernomorsky |
| 2015/0051482 A1 | 2/2015 | Liu et al. |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0073267 A1 | 3/2015 | Brannan et al. |
| 2015/0088161 A1 | 3/2015 | Hata et al. |
| 2015/0104284 A1 | 4/2015 | Riedel et al. |
| 2015/0119628 A1 | 4/2015 | Bharat et al. |
| 2015/0119645 A1 | 4/2015 | Baldwin |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0150635 A1 | 6/2015 | Kilroy et al. |
| 2015/0150636 A1 | 6/2015 | Hagn et al. |
| 2015/0202015 A1 | 7/2015 | Elhawary et al. |
| 2015/0223725 A1 | 8/2015 | Engel et al. |
| 2015/0223832 A1 | 8/2015 | Swaney et al. |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Messick, Jr. |
| 2015/0265359 A1 | 9/2015 | Camarillo |
| 2015/0265368 A1* | 9/2015 | Chopra ............ A61B 1/000094 600/587 |
| 2015/0265807 A1 | 9/2015 | Park et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0297299 A1 | 10/2015 | Yeung et al. |
| 2015/0311838 A1 | 10/2015 | Moule et al. |
| 2015/0313503 A1 | 11/2015 | Seibel et al. |
| 2015/0342695 A1 | 12/2015 | He et al. |
| 2015/0359597 A1 | 12/2015 | Gombert et al. |
| 2016/0000302 A1 | 1/2016 | Brown et al. |
| 2016/0000414 A1 | 1/2016 | Brown et al. |
| 2016/0000495 A1 | 1/2016 | Elliott et al. |
| 2016/0000520 A1 | 1/2016 | Achmanovich et al. |
| 2016/0001038 A1 | 1/2016 | Romo et al. |
| 2016/0005168 A1 | 1/2016 | Merlet |
| 2016/0005220 A1 | 1/2016 | Weingarten et al. |
| 2016/0005576 A1 | 1/2016 | Tsukamoto |
| 2016/0008033 A1 | 1/2016 | Hawkins et al. |
| 2016/0016319 A1 | 1/2016 | Remirez et al. |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper et al. |
| 2016/0075030 A1 | 3/2016 | Takahashi et al. |
| 2016/0081568 A1 | 3/2016 | Kolberg et al. |
| 2016/0100772 A1 | 4/2016 | Kuma et al. |
| 2016/0111192 A1 | 4/2016 | Suzara |
| 2016/0128781 A1 | 5/2016 | Blohm et al. |
| 2016/0128992 A1 | 5/2016 | Hudson et al. |
| 2016/0135908 A1 | 5/2016 | Takahashi et al. |
| 2016/0166320 A1 | 6/2016 | Ciulla et al. |
| 2016/0183841 A1 | 6/2016 | Duindam et al. |
| 2016/0199134 A1 | 7/2016 | Brown et al. |
| 2016/0206389 A1 | 7/2016 | Miller et al. |
| 2016/0213432 A1 | 7/2016 | Flexman et al. |
| 2016/0228032 A1 | 8/2016 | Walker et al. |
| 2016/0249990 A1* | 9/2016 | Glozman ............ A61B 34/30 606/130 |
| 2016/0270865 A1 | 9/2016 | Andey et al. |
| 2016/0278865 A1 | 9/2016 | Capote et al. |
| 2016/0287053 A1 | 10/2016 | Miura et al. |
| 2016/0287111 A1 | 10/2016 | Jacobsen et al. |
| 2016/0287279 A1 | 10/2016 | Bovay et al. |
| 2016/0287346 A1 | 10/2016 | Hyodo et al. |
| 2016/0314710 A1 | 10/2016 | Jarc et al. |
| 2016/0331469 A1 | 11/2016 | Hall et al. |
| 2016/0338787 A1 | 11/2016 | Popovic et al. |
| 2016/0346038 A1 | 12/2016 | Helgeson et al. |
| 2016/0346924 A1 | 12/2016 | Hasegawa et al. |
| 2016/0354057 A1 | 12/2016 | Hansen et al. |
| 2016/0360947 A1 | 12/2016 | Iida et al. |

(56) References Cited

U.S. PATENT DOCUMENTS

| | | |
|---|---|---|
| 2016/0360949 A1 | 12/2016 | Hyodo et al. |
| 2016/0372743 A1 | 12/2016 | Cho et al. |
| 2017/0000574 A1 | 1/2017 | Itkowitz et al. |
| 2017/0007337 A1 | 1/2017 | Dan |
| 2017/0023423 A1 | 1/2017 | Jackson et al. |
| 2017/0055851 A1 | 3/2017 | Al-Ali et al. |
| 2017/0056215 A1 | 3/2017 | Nagesh et al. |
| 2017/0068796 A1 | 3/2017 | Passerini et al. |
| 2017/0071456 A1 | 3/2017 | Ratnakar |
| 2017/0079725 A1 | 3/2017 | Hoffman et al. |
| 2017/0079726 A1 | 3/2017 | Hoffman et al. |
| 2017/0084027 A1 | 3/2017 | Mintz et al. |
| 2017/0095299 A1 | 4/2017 | Hendrick et al. |
| 2017/0100197 A1 | 4/2017 | Zubiate et al. |
| 2017/0106904 A1 | 4/2017 | Hanson et al. |
| 2017/0119412 A1 | 5/2017 | Noonan et al. |
| 2017/0119474 A1 | 5/2017 | Kronman |
| 2017/0119481 A1 | 5/2017 | Romo et al. |
| 2017/0135710 A1 | 5/2017 | Hasegawa et al. |
| 2017/0135718 A1 | 5/2017 | Lyons |
| 2017/0135833 A1 | 5/2017 | Syed |
| 2017/0143442 A1 | 5/2017 | Tesar et al. |
| 2017/0165503 A1 | 6/2017 | Hautvast et al. |
| 2017/0181809 A1 | 6/2017 | Panescu et al. |
| 2017/0189118 A1 | 7/2017 | Chopra et al. |
| 2017/0189131 A1 | 7/2017 | Weir |
| 2017/0202624 A1 | 7/2017 | Atarot et al. |
| 2017/0202627 A1 | 7/2017 | Sramek et al. |
| 2017/0209073 A1 | 7/2017 | Sramek et al. |
| 2017/0209162 A1 | 7/2017 | Sperry et al. |
| 2017/0215808 A1 | 8/2017 | Shimol et al. |
| 2017/0215969 A1 | 8/2017 | Zhai et al. |
| 2017/0231647 A1 | 8/2017 | Saunders et al. |
| 2017/0238807 A9 | 8/2017 | Vertikov |
| 2017/0245854 A1 | 8/2017 | Zemlok et al. |
| 2017/0245885 A1 | 8/2017 | Enker et al. |
| 2017/0251988 A1 | 9/2017 | Weber et al. |
| 2017/0258366 A1 | 9/2017 | Tupin, Jr. et al. |
| 2017/0280978 A1 | 10/2017 | Yamamoto et al. |
| 2017/0281049 A1 | 10/2017 | Yamamoto et al. |
| 2017/0290631 A1 | 10/2017 | Lee et al. |
| 2017/0296032 A1 | 10/2017 | Li |
| 2017/0296202 A1 | 10/2017 | Brown |
| 2017/0303889 A1 | 10/2017 | Grim et al. |
| 2017/0303941 A1 | 10/2017 | Eisner |
| 2017/0304015 A1 | 10/2017 | Tavallaei et al. |
| 2017/0325715 A1 | 11/2017 | Mehendale et al. |
| 2017/0325896 A1 | 11/2017 | Donhowe et al. |
| 2017/0326337 A1 | 11/2017 | Romoscanu et al. |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2018/0025666 A1 | 1/2018 | Ho et al. |
| 2018/0036033 A1* | 2/2018 | Ignagni ............... A61B 5/24 |
| 2018/0055576 A1 | 3/2018 | Koyrakh et al. |
| 2018/0055582 A1 | 3/2018 | Krimsky |
| 2018/0064498 A1 | 3/2018 | Kapadia et al. |
| 2018/0098690 A1 | 4/2018 | Iwaki |
| 2018/0098817 A1 | 4/2018 | Nichogi |
| 2018/0169671 A1 | 6/2018 | Winter et al. |
| 2018/0199999 A1* | 7/2018 | Syverson ............... A61B 34/30 |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0263568 A1 | 9/2018 | Yi et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289394 A1 | 10/2018 | Shah |
| 2018/0289431 A1 | 10/2018 | Draper et al. |
| 2018/0296281 A1 | 10/2018 | Yeung et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0338799 A1 | 11/2018 | Hladio et al. |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000568 A1* | 1/2019 | Connolly ............... A61B 90/90 |
| 2019/0000576 A1 | 1/2019 | Mintz et al. |
| 2019/0046814 A1 | 2/2019 | Senden et al. |
| 2019/0066314 A1 | 2/2019 | Abhari et al. |
| 2019/0083183 A1 | 3/2019 | Moll et al. |
| 2019/0083187 A1* | 3/2019 | Danitz ................... A61B 34/32 |
| 2019/0086349 A1 | 3/2019 | Nelson et al. |
| 2019/0110839 A1 | 4/2019 | Rafii-Tari et al. |
| 2019/0125164 A1 | 5/2019 | Roelle et al. |
| 2019/0139216 A1* | 5/2019 | Georgescu ............. G06N 3/048 |
| 2019/0151148 A1 | 5/2019 | Alvarez et al. |
| 2019/0167366 A1 | 6/2019 | Ummalaneni et al. |
| 2019/0167367 A1 | 6/2019 | Walker et al. |
| 2019/0175009 A1 | 6/2019 | Mintz et al. |
| 2019/0175062 A1 | 6/2019 | Rafii-Tari et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0201106 A1 | 7/2019 | Siemionow et al. |
| 2019/0209252 A1 | 7/2019 | Walker et al. |
| 2019/0216548 A1 | 7/2019 | Ummalaneni |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0246882 A1 | 8/2019 | Graetzel et al. |
| 2019/0262084 A1 | 8/2019 | Roh et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0008874 A1 | 1/2020 | Barbagli et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0078103 A1 | 3/2020 | Duindam et al. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Eparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0155084 A1 | 5/2020 | Walker et al. |
| 2020/0170630 A1 | 6/2020 | Wong et al. |
| 2020/0170720 A1 | 6/2020 | Ummalaneni |
| 2020/0171660 A1 | 6/2020 | Ho et al. |
| 2020/0188043 A1 | 6/2020 | Yu et al. |

(56) References Cited

U.S. PATENT DOCUMENTS

| | | |
|---|---|---|
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0246591 A1 | 8/2020 | Bogusky |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0305922 A1 | 10/2020 | Yan et al. |
| 2020/0305983 A1 | 10/2020 | Yampolsky et al. |
| 2020/0305989 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2021/0196312 A1 | 7/2021 | Plewe et al. |
| 2021/0196399 A1 | 7/2021 | Plewe |
| 2022/0371202 A1 | 11/2022 | Schoessler et al. |
| 2023/0363635 A1 | 11/2023 | Ayvali et al. |

FOREIGN PATENT DOCUMENTS

| | | |
|---|---|---|
| CN | 1846181 A | 10/2006 |
| CN | 1857877 A | 11/2006 |
| CN | 101147676 A | 3/2008 |
| CN | 101222882 A | 7/2008 |
| CN | 102316817 A | 1/2012 |
| CN | 101325920 B | 2/2012 |
| CN | 102341057 A | 2/2012 |
| CN | 102458295 A | 5/2012 |
| CN | 102973317 A | 3/2013 |
| CN | 103565529 A | 2/2014 |
| CN | 103705307 A | 4/2014 |
| CN | 103735313 A | 4/2014 |
| CN | 102458295 B | 6/2014 |
| CN | 103930063 A | 7/2014 |
| CN | 102711586 B | 6/2015 |
| CN | 103767659 B | 6/2015 |
| CN | 105030331 A | 11/2015 |
| CN | 105208960 A | 12/2015 |
| CN | 105511881 A | 4/2016 |
| CN | 105559850 A | 5/2016 |
| CN | 105559886 A | 5/2016 |
| CN | 106097353 A | 11/2016 |
| CN | 104758066 B | 5/2017 |
| CN | 105559850 B | 8/2017 |
| CN | 107028659 A | 8/2017 |
| CN | 103813748 B | 4/2018 |
| CN | 107997778 A | 5/2018 |
| CN | 108348139 A | 7/2018 |
| CN | 108430373 A | 8/2018 |
| CN | 104931059 B | 9/2018 |
| CN | 104684502 B | 10/2018 |
| CN | 109753866 A | 5/2019 |
| CN | 106821498 B | 2/2020 |
| DE | 102013100605 A1 | 7/2014 |
| EP | 0347098 B1 | 2/1996 |
| EP | 1250986 A2 | 10/2002 |
| EP | 1566150 A2 | 8/2005 |
| EP | 1800593 A1 | 6/2007 |
| EP | 2158834 A1 | 3/2010 |
| EP | 2392435 A2 | 12/2011 |
| EP | 2615992 A2 | 7/2013 |
| EP | 3025630 A1 | 6/2016 |
| JP | 2008528130 A | 7/2008 |
| JP | 2009509654 A | 3/2009 |
| JP | 2009524530 A | 7/2009 |
| JP | 2011088260 A | 5/2011 |
| JP | 2013510662 A | 3/2013 |
| JP | 2016526958 A | 9/2016 |
| JP | 2016529999 A | 9/2016 |
| JP | 2019505245 A | 2/2019 |
| JP | 2019508072 A | 3/2019 |
| JP | 2021525584 A | 9/2021 |
| KR | 1020140009359 A | 1/2014 |
| KR | 20180084751 A | 7/2018 |
| RU | 2569699 C2 | 11/2015 |
| WO | 0156457 A1 | 8/2001 |
| WO | 2004029782 A2 | 4/2004 |
| WO | 2005078128 A1 | 8/2005 |
| WO | 2006122061 A1 | 11/2006 |
| WO | 2009097461 A1 | 8/2009 |
| WO | 2009120940 A2 | 10/2009 |
| WO | 2010127162 A1 | 11/2010 |
| WO | 2011002215 A3 | 4/2011 |
| WO | 2011132409 A1 | 10/2011 |
| WO | 2012044334 A2 | 4/2012 |
| WO | 2012082719 A1 | 6/2012 |
| WO | 2014114551 A1 | 7/2014 |
| WO | 2014186715 A1 | 11/2014 |
| WO | 2015023665 A1 | 2/2015 |
| WO | 2015089013 A1 | 6/2015 |
| WO | 2015142957 A1 | 9/2015 |
| WO | 2016142693 A1 | 9/2016 |
| WO | 2017036774 A1 | 3/2017 |
| WO | 2017048194 A1 | 3/2017 |
| WO | 2017053698 A1 | 3/2017 |
| WO | 2017066108 A1 | 4/2017 |
| WO | 2017075085 A1 | 5/2017 |
| WO | 2017075574 A1 | 5/2017 |
| WO | 2017146890 A1 | 8/2017 |
| WO | 2017167754 A1 | 10/2017 |
| WO | 2018098477 A1 | 5/2018 |
| WO | 2018144636 A1 | 8/2018 |
| WO | 2018160288 A1 | 9/2018 |
| WO | 2019174953 A1 | 9/2019 |
| WO | 2019210322 A1 | 10/2019 |
| WO | 2021198906 A1 | 10/2021 |

OTHER PUBLICATIONS

JP Examination Report for Application No. 2022-540385, dated Aug. 28, 2024, 37-pages with translation.
CN Office Action for Appl. No. 202080091098.X, dated Jan. 26, 2024, 8 pages.
CN Office Action for Appl. No. 202080091098X, dated Feb. 22, 2023, 16 pages.
EP Search Report for Appl. No. 20910116.1, dated Dec. 4, 2023, 9 pages.
Al-Ahmad et al., dated 2005, Early experience with a computerized robotically controlled catheter system, Journal of Interventional Cardiac Electrophysiology, 12:199-202, 4 pages.
Blankenstein, Jun. 2008, Dynamic Registration and High Speed Visual Servoing in Robot-Assisted Surgery, Katholieke Universiteit Leuven, Leuven, Belgium, 96 pages.
Ciuti et al., 2012, Intra-Operative Monocular 3D Reconstruction for Image-Guided Navigation in Active Locomotion Capsule Endoscopy. Biomedical Robotics and Biomechatronics (Biorob), 4th IEEE Ras & Embs International Conference on IEEE, 7 pages.
Darwiche, 2015, Operative technique and early experience for robotic assisted laparoscopic nephroureterectomy (RALNU) using da Vinci XI, SpringerPlus, 4:298, 5 pages.
Fallavoliita et al., 2010, Acquiring Multiview C-Arm Images to Assist Cardiac Ablation Procedures, EURASIP Journal on Image and Video Processing, vol. 2010, Article ID 871408, pp. 1-10.
Final Rejection for U.S. Appl. No. 17/120,790, dated Aug. 27, 2021, 8 pages.
Gutierrez et al., Mar. 2008, A Practical Global Distortion Correction Method for an Image Intensifier Based X-Ray Fluoroscopy System, Med. Phys, 35(3):997-1007, 11 pages.
Haigron et al., 2004, Depth-map-based scene analysis for active navigation in virtual angioscopy, IEEE Transactions on Medical Imaging, 23( 11 ): 1380-1390, 11 pages.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).

(56) References Cited

OTHER PUBLICATIONS

Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pages.
Hansen Medical, Inc. dated 2009, Sensei X Robotic Catheter System, product brochure, 3 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
He, Kaiming, Georgia Gkioxari, Piotr Dollar, and Ross Girshick. "Mask R-cnn." In Computer Vision (ICCV), 2017 IEEE International Conference on. IEEE, 2017. 12 pages.
International Preliminary Report on Patentability and Written Opinion for Appl. No. PCT/IB2020/061908, dated Jul. 5, 2022, 6 pages.
International search report and written opinion dated Dec. 18, 2019 for PCT/US2019/53600, 13 pages.
Kiraly et al., 2002, Three-dimensional Human Airway Segmentation Methods for Clinical Virtual Bronchoscopy, Acad Radio!, 9:1153-1168, 16 pages.
Kiraly et al., Sep. 2004, Three-dimensional path planning for virtual bronchoscopy, IEEE Transactions on Medical Imaging, 23(9):1365-1379, 15 pages.
Konen et al., 1998, The VN-project endoscopic image processing for neurosurgery, Computer Aided Surgery, 3:1-6 6 pages.
Kukuk, Oct. 5, 2001, TBNA-protocols: Guiding TransBronchial Needle Aspirations Without a Computer in the Operating Room, MICCAI 2001, 2208:997-1006.
Kumar et al., 2014, Stereoscopic visualization of laparoscope image using depth information from 3D model, Computer methods and programs in biomedicine 113(3):862-868, 7 pages.
Lawton et al., 1999, Ribbons and groups: A thin rod theory for catheters and filaments, J. Phys. A., 1999, 32:1709-1735, 27 pages.
Livatino et al., 2015, Stereoscopic visualization and 3-D technologies in medical endoscopic teleoperation, IEEE, 11 pages.
Luo et al., 2010, Modified hybrid bronchoscope tracking based on sequential monte carlo sampler: Dynamic phantom validation, Asian Conference on Computer Vision. Springer, Berlin, Heidelberg, 13 pages.
Marrouche et al., dated May 6, 2005, AB32-1, Preliminary human experience using a novel robotic catheter remote control, Heart Rhythm, 2(5):S63, 1 page.
Mayo Clinic, Robotic Surgery, https://www.mayoclinic.org/tests-procedures/robotic-surgery/about/pac- 20394974?p=1, downloaded from the internet on Jul. 12, 2018, 2 pgs.
Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.
Nadeem et al., 2016, Depth Reconstruction and Computer-Aided Polyp Detection in Optical Colonoscopy Video Frames, arXiv preprint arXiv:1609.01329, 12 pages.
Non Final Rejection for U.S. Appl. No. 17/120,790, dated May 20, 2021, 13 pages.
Notice of Allowance for U.S. Appl. No. 17/120,790, dated Dec. 8, 2021, 8 pages.
Notice of Allowance for U.S. Appl. No. 17/120,790, dated Jan. 18, 2022, 5 pages.
Oh et al., dated May 2005, P5-75, Novel robotic catheter remote control system: safety and accuracy in delivering RF esions in all 4 cardiac chambers, Heart Rhythm, 2(5):S277-S278.
Point Cloud, Sep. 10, 2010, Wikipedia, 2 pp.
Racadio et al., Dec. 2007, Live 3D guidance in the interventionail radiology suite, AJR, 189:W357-W364, 8 pages.
Reddy et al., May 2005, P1-53. Porcine pulmonary vein ablation using a novel robotic catheter control system and real- time integration of CT imaging with electroanatomical mapping, Hearth Rhythm, 2(5):S121, 1 page.
Sasaki, 2017, Laparoscopic hemicolectomy for a patient with situs inversus totalis: a case report, Int. J. Surg. Case Rep. 41 :93-96, 4 pages.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813, 13 pages.
Shi et al., Sep. 14-18, 2014, Simultaneous catheter and environment modeling for trans-catheter aortic valve Implantation, IEEE/RSJ International Conference on Intelligent Robots and Systems, pp. 2024-2202.
Slepian, dated 2010, Robotic Catheter Intervention: the Hansen Medical Sensei Robot Catheter System, PowerPoint presentation, 28 pages.
Solheim et ai., May 14, 2009, Navigated resection of giant intracranial meningiomas based on intraoperative 30 ultrasound, Acta Neurochir, 151:1143-1151.
Solomon et al., Dec. 2000, Three-dimensional CT- Guided Bronchoscopy With a Real-Time Electromagnetic Position Sensor a Comparison of Two Image Registration Methods, Chest, 118(6):1783-1787.
Song et al., 2012, Autonomous and stable tracking of endoscope instrument tools with monocular camera, Advanced Intelligent Mechatronics (AIM), 2012 IEEE-ASME International Conference on.IEEE, 6 pages.
Vemuri et al., Dec. 2015, Inter-operative biopsy site relocations in endoluminal surgery, IEEE Transactions on Biomedical Engineering, Institute of Electrical and Electronics Engineers, < 10 1109/T8ME 2015.2503981 >, 13 pages.
Verdaasdonk et al., Jan. 23, 2012, Effect of Microsecond Pulse Length and Tip Shape on Explosive Bubble Formation of 2.78 µm Er, Cr; YSGG and 2.94 µm Er:YAG laser, Proceedings of SPIE, vol. 8221, 12, 1 pages.
Wilson et al., 2008, A Buyer's Guide to Electromagnetic Tracking Systems for Clinical Applications, Proc. of SPCI, 6918:691828-1, 12 pages.
Yip et al., 2012, Tissue tracking and registration for image-guided surgery, IEEE transactions on medical imaging 31(11 ):2169-2182, 14 pages.
Zhou et al., 2010, Synthesis of stereoscopic views from monocular endoscopic videos, Compute Vision and Pattern Recognition Workshops (CVPRVV), 2010 IEEE Computer Society Conference on IEE, 8 pages.
CN 2nd Office Action for Appl. No. 202080091098, dated Sep. 14, 2023, 7 pages.
EP Examination Report for Appl. No. 20910116.1, dated Aug. 16, 2024, 4 pages.
JP Office Action for Application No. 2022-540385, dated Sep. 24, 2024, 11-pages with translation.
Non-Final Rejection from U.S. Appl. No. 17/208,874, dated Feb. 2, 2023, 8 pages.
Notice of Allowance from U.S. Appl. No. 17/208,874 dated Apr. 13, 2023, 8 pages.
International Search Report from PCT Application No. PCTIB2021052625, dated Jul. 2, 2021, 5 pages.
International Written Opinion from PCT Application No. PCT/IB2021/052625, dated Jul. 2, 2021, 6 pages.
Search Report from European Patent Application No. 21782289.9, dated Mar. 5, 2024, 9 pages.
Office Action from Japanese Patent Application No. 2022-559640, issued on Oct. 15, 2024, pp. 1-11.
Examination Report from European Patent Application No. 21782289.9, mailed on Dec. 10, 2024, pp. 1-3.
International Search Report and Written Opinion from PCT Application No. PCT/IB2025/052948, dated Jun. 27, 2025, 12 pages.

* cited by examiner

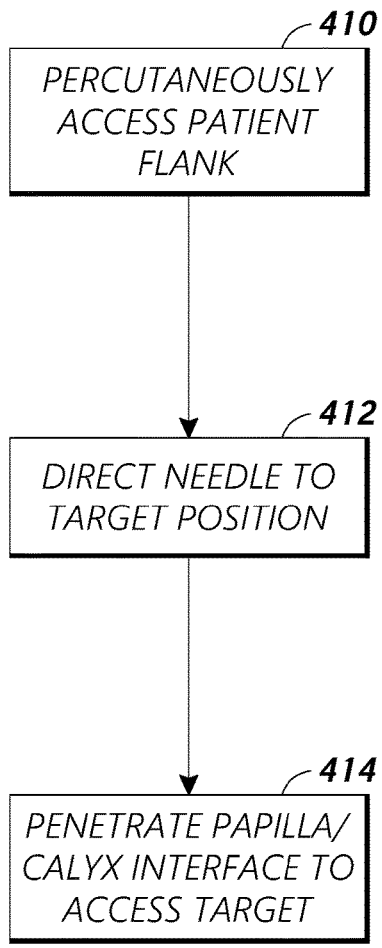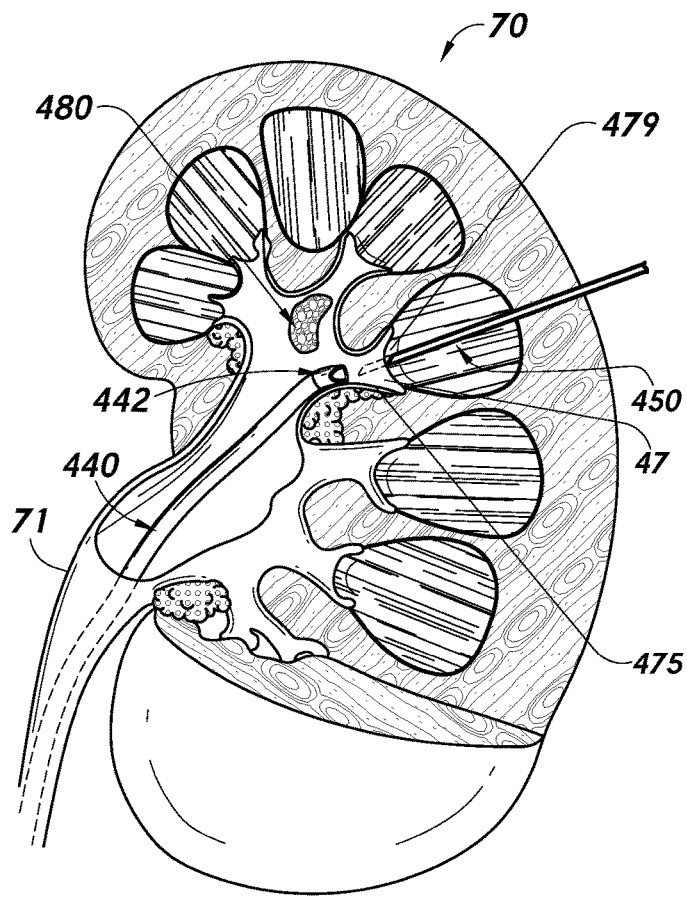
FIG. 4-2                FIG. 5-2

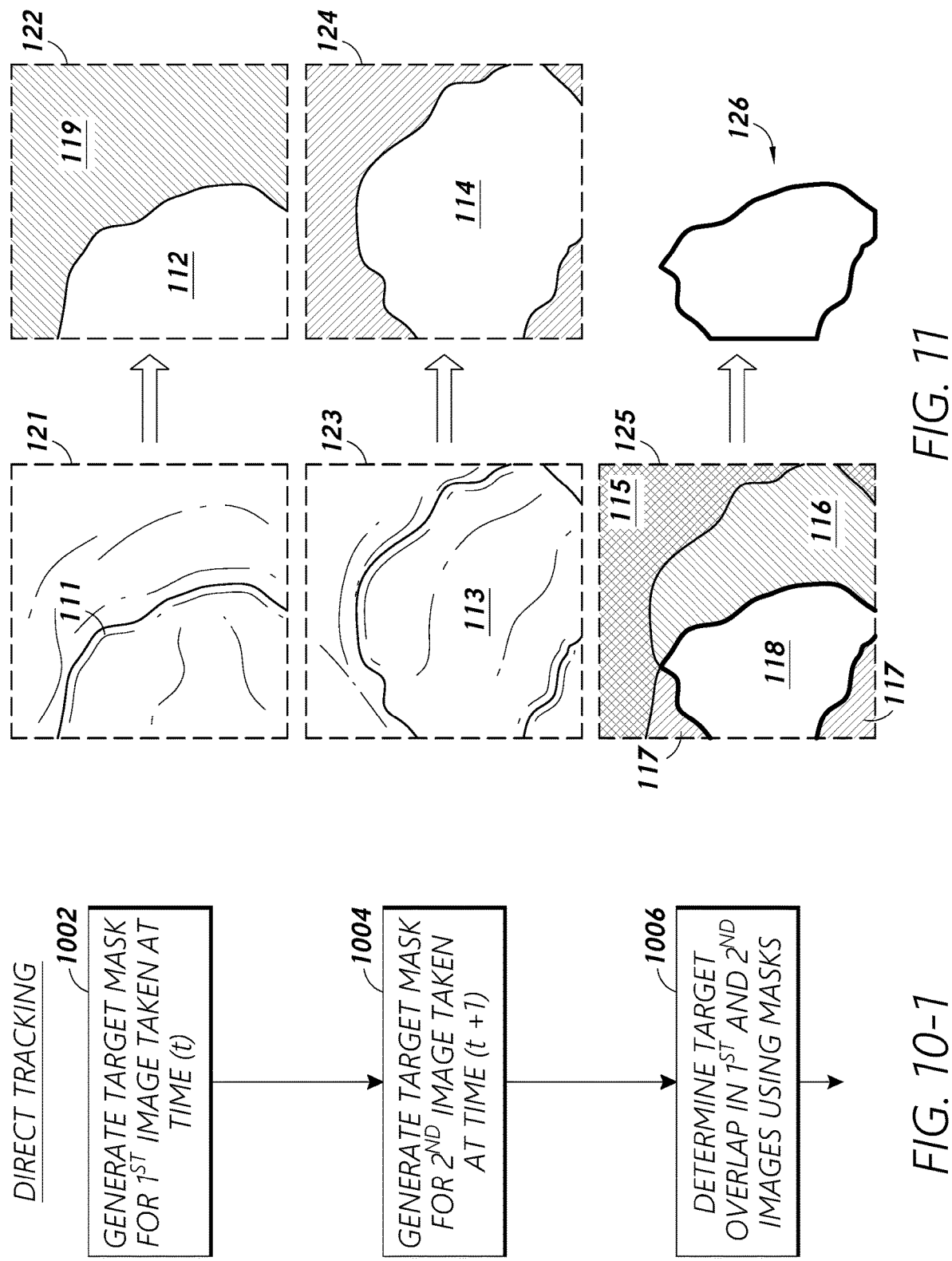

ANATOMICAL FEATURE TRACKING

RELATED APPLICATION(S)

This application is a continuation of U.S. application Ser. No. 17/120,790, filed Dec. 14, 2020, and entitled "ANATOMICAL FEATURE IDENTIFICATION AND TARGETING," now U.S. Pat. No. 11,298,195, which claims priority to U.S. Prov. App. No. 62/955,991, filed Dec. 31, 2019, and entitled "ANATOMICAL FEATURE IDENTIFICATION AND TARGETING," the disclosures of which are hereby incorporated by reference in their entirety.

BACKGROUND

Field

The present disclosure relates to the field of medical procedures.

Description of Related Art

Various medical procedures involve the use of one or more scope-type devices configured with certain image-capturing functionality, which may be utilized to provide visualization of certain anatomical features associated with the respective medical procedure. Certain operational processes can be guided at least in part by image data captured using such devices.

SUMMARY

Described herein are systems, devices, and methods to facilitate the identification and tracking of various anatomical features based on images of such features obtained using a scope device or other medical instrument. Such feature identification and/or tracking can facilitate the targeting of certain anatomical features in connection with a medical procedure, such as nephroscopy or other procedure accessing the renal anatomy, for example.

In some implementations, the present disclosure relates to a method of positioning a surgical instrument. The method comprises advancing a first medical instrument to a treatment site of a patient, the first medical instrument comprising a camera, recording a target position associated with a target anatomical feature at the treatment site, generating a first image of the treatment site using the camera of the first medical instrument, identifying the target anatomical feature in the first image using a pretrained neural network, and adjusting the target position based at least in part on a position of the identified target anatomical feature in the first image.

The method can further comprise adjusting an orientation of the first medical instrument based at least in part on the position of the identified target anatomical feature in the first image. For example, adjusting the orientation of the first medical instrument can involve centering the identified target anatomical feature in a field of view associated with the camera.

In some embodiments, recording the target position involves contacting the target anatomical feature with a distal end of the first medical instrument, generating position data indicating a contact position of the target anatomical feature and the distal end of the first medical instrument, and causing the position data to be stored in one or more data storage devices. For example, the method can further comprise retracting the distal end of the first medical instrument away from the target anatomical feature prior to said generating the first image.

In some embodiments, the method further comprises generating a second image of the treatment site using the camera of the first medical instrument after generating the first image, identifying an anatomical feature in the second image using the pretrained neural network, determining that the anatomical feature of the second image and the target anatomical feature of the first image represent the same feature, and in response to said determining, adjusting the target position based at least in part on a position of the identified anatomical feature in the second image. For example, determining that the anatomical feature of the second image and the target anatomical feature of the first image represent the same feature can involve determining an amount of overlap between at least a portion of the anatomical feature of the second image and at least a portion of the target anatomical feature of the first image and determining that the amount of overlap is greater than a predetermined threshold. The method may further comprise generating a first mask of the first image that masks the at least a portion of the target anatomical feature of the first image and generating a second mask of the second image that masks the at least a portion of the anatomical feature of the second image, wherein determining the amount of overlap is performed using the first mask and the second mask. In some embodiments, determining that the anatomical feature of the second image and the target anatomical feature of the first image represent the same feature can involve tracking movement of a feature between the first image and the second image. In some embodiments, the method further comprises estimating a three-dimensional position of the anatomical feature of the second image based at least in part on the first image and the second image. For example, estimating the three-dimensional position of the anatomical feature is based on one or more of: camera focal length, camera principal point, relative motion of the first medical instrument, rotation of the first medical instrument, and electromagnetic, structured lighting, and/or time-of-flight sensor readings.

In some embodiments, adjusting the target position is further based at least in part on determined movement of the first medical instrument. The method can further comprise percutaneously directing a second medical instrument through tissue of the patient towards the target position. For example, directing the second medical instrument through the tissue of the patient towards the target position can be performed using sensor data provided by alignment sensors of both the first medical instrument and the second medical instrument. In some embodiments, the method is performed at least in part by a robotic system.

In some implementations, the present disclosure relates to a method of targeting an anatomical feature. The method comprises receiving target position data indicating a target position associated with a target anatomical feature of a patient, storing the target position data in one or more data storage devices, receiving a first image of a surgical site within a patient, using an artificial neural network to identify a first form in the first image that represents the target anatomical feature, and storing updated target position data indicating the target position based on the identified form in the first image.

The method can further comprise causing a medical instrument to be articulated in response to the updated target position data. In some embodiments, the method is performed by control circuitry of a medical system and the target position data and the first image are received from an endoscope of the medical system. The target anatomical feature can be an exposed portion of a papilla within a calyx of a kidney of the patient. The artificial neural network can be pretrained based on known image and label data. For example, the artificial neural network can include a multiple-layer feature pyramid network.

The updated target position data can be based at least in part on known respiratory information relating to the patient. In some embodiments, the method further comprises receiving a second image of the surgical site, using the artificial neural network to identify a second form in the second image that represents the target anatomical feature, and determining a three-dimensional position of the target anatomical feature based at least in part on the first form and the second form. For example, determining the three-dimensional position of the target anatomical feature can be based at least in part on a relative size of the second form. In some embodiments, determining the three-dimensional position of the target anatomical feature is based on data generated by one or more external camera sensors, such as structured lighting sensor(s), time-of-flight sensor(s), and/or the like.

In some implementations, the present disclosure relates to a medical system that comprises an endoscope having a camera and an electromagnetic position sensor associated with a distal end thereof, a robotic medical subsystem including a plurality of articulating arms, and control circuitry communicatively coupled to the endoscope and the robotic medical subsystem. The control circuitry is configured to advance the endoscope to a treatment site of a patient in response to user input, record a position of the distal end of the endoscope within an electromagnetic field, generate user interface data indicating the position as a target anatomical position, receive a first image from the camera of the endoscope, identify a target anatomical feature in the first image using a pretrained neural network, and adjust the target anatomical position based at least in part on a position of the identified target anatomical feature in the first image.

The control circuitry can be further configured to calibrate the distal end of the endoscope in the electromagnetic field. In some embodiments, the medical system further comprises a robotic nephroscope communicatively coupled to the control circuitry.

In some implementations, the present disclosure relates to a computing device comprising an endoscope interface and control circuitry comprising one or more processors and one or more data storage devices. The control circuitry is configured to receive alignment sensor data indicating a position of a distal end of an endoscope coupled to the control circuitry over the endoscope interface, generate first user interface data indicating the position of the distal end of the endoscope as a target nephroscopy position, receive a first image of a medical site over the endoscope interface, identify a first anatomical form in the first image, receive a second image of the medical site over the endoscope interface, identify a second anatomical form in the second image, determine that the first anatomical form and the second anatomical form represent the same target anatomical feature, and update the target nephroscopy position based on said determining.

The control circuitry can be further configured to determine that an amount of overlap of the first form and the second form in an overlay of the first and second images is greater than a predetermined threshold. In some embodiments, the control circuitry is configured to, in response to said updating the target nephroscopy position, generate second user interface data indicating the updated target nephroscopy position.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 4-1 and 4-2 provide a flow diagram illustrating a process for performing guided percutaneous nephrolithotomy in accordance with one or more embodiments.

FIGS. 5-1 and 5-2 show certain images corresponding to various blocks, states, and/or operations associated with the process of FIG. 4 in accordance with one or more embodiments.

FIGS. 10-1 and 10-2 provide a flow diagram illustrating a process for tracking a target anatomical feature in accordance with one or more embodiments.

FIG. 11 shows certain images corresponding to various blocks, states, and/or operations associated with the process of FIGS. 10-1 and 10-2 in accordance with one or more embodiments.

DETAILED DESCRIPTION

Figure 1:
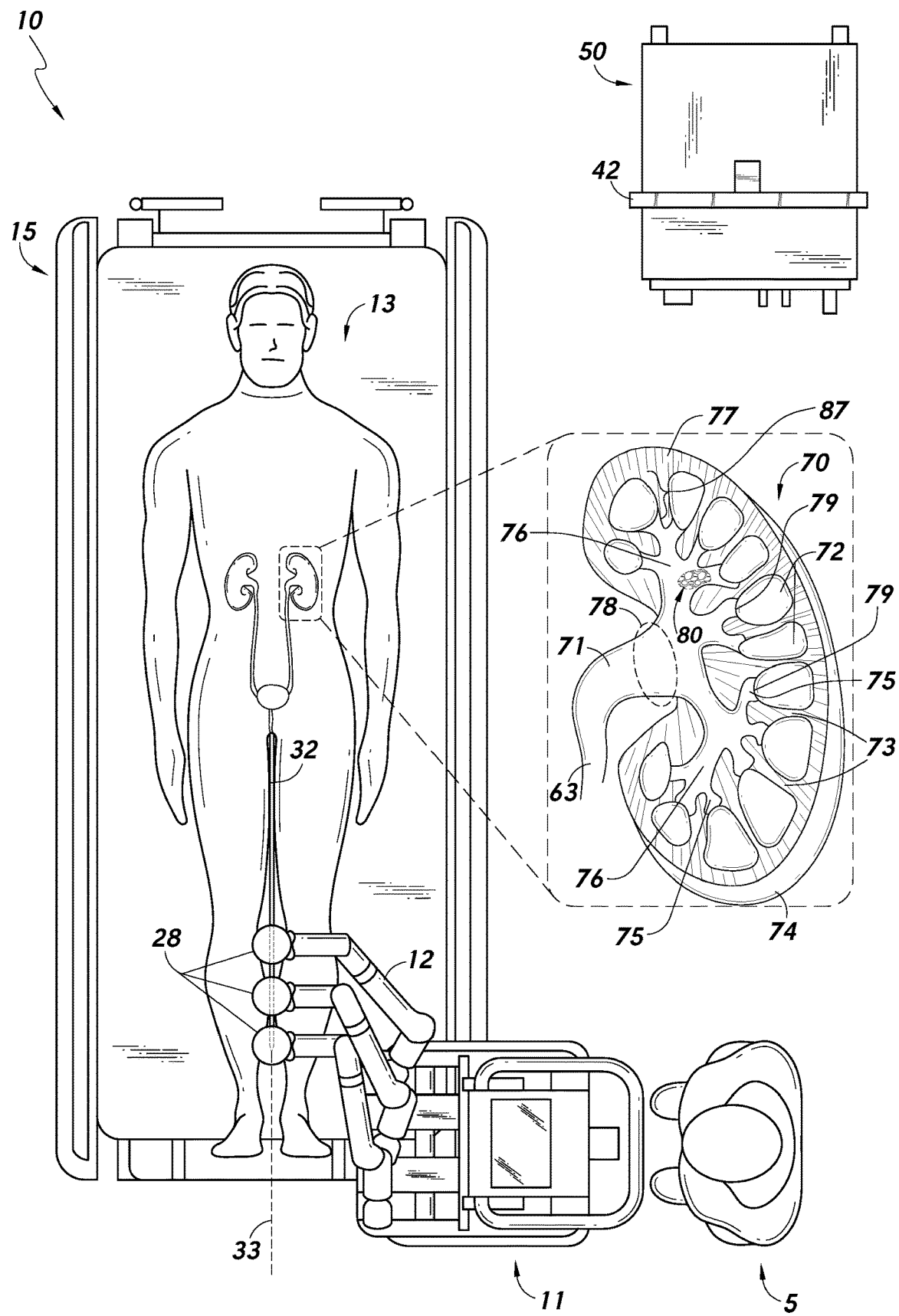
FIG. 1 illustrates an embodiment of a robotic medical system in accordance with one or more embodiments.

The headings provided herein are for convenience only and do not necessarily affect the scope or meaning of the claimed invention. Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location are used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/ element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

The present disclosure relates to systems, devices, and methods for identifying and tracking target anatomical features of a patient to aid in certain medical procedures. Although certain aspects of the present disclosure are described in detail herein in the context of renal, urological, and/or nephrological procedures, such as kidney stone removal/treatment procedures, it should be understood that such context is provided for convenience and clarity, and anatomical feature identification and tracking concepts disclosed herein are applicable to any suitable medical procedures. However, as mentioned, description of the renal/ urinary anatomy and associated medical issues and procedures is presented below to aid in the description of the inventive concepts disclosed herein.

Kidney stone disease, also known as urolithiasis, is a relatively common medical condition involves the formation in the urinary tract of a solid piece of material, referred to as "kidney stones," "urinary stones," "renal calculi," "renal lithiasis," or "nephrolithiasis." Urinary stones may be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones may be formed from calcium, magnesium, ammonia, ur acid, cysteine, and/or other compounds.

To remove urinary stones from the bladder and ureter, surgeons may a ureteroscope inserted into the urinary tract through the urethra. Typically, a ureteroscope includes an endoscope at its distal end configured to enable visualization of the urinary tract. The ureteroscope can also include a lithotomy mechanism to capture or break apart urinary stones. During a ureteroscopy procedure, one physician/ technician may control the position of the ureteroscope, while another other physician/technician may control the lithotomy mechanism.

In order to remove relatively large stones from the kidneys (i.e., "kidney stones"), physicians may use a percutaneous nephrolithotomy ("PCNL") technique that includes inserting a nephroscope through the skin to break up and/or remove the stone(s). Locating the kidney stone(s) may be achieved using fluoroscopy to provide a target for insertion of the nephroscope. However, fluoroscopy increases the cost of the nephrolithotomy procedure due to the cost of the fluoroscope itself as well as the cost of a technician to operate the fluoroscope. Fluoroscopy also exposes the patient to radiation for a prolonged period of time. Even with fluoroscopy, accurately making a percutaneous incision to access the kidney stone can be difficult and undesirably imprecise. Furthermore, some nephrolithotomy techniques involve a two-day or three-day inpatient stay. In sum, certain nephrolithotomy techniques can be relatively costly and problematic for patients.

According to certain surgical procedures, endoscopes (e.g., ureteroscopes) can be equipped with position sensors, wherein the position of the sensors is used as a target for percutaneous access, such as for PCNL. For example, an electromagnetic-sensor-equipped ureteroscope and/or an electromagnetic-sensor-equipped percutaneous access needle may be used to guide the percutaneous renal access for kidney stone removal and/or the like. In such procedures, the surgeon/physician can drive the ureteroscope to a target calyx of the kidney and use an electromagnetic sensor (e.g., beacon) associated with a distal end/tip of the ureteroscope as the percutaneous access target for the needle. Generally, the efficacy of percutaneous axis to a target calyx can depend at least in part on where the physician positions/parks the ureteroscope with respect to, for example, the position and/or heading of the ureteroscope relative to a papilla through which percutaneous access may be made to the target calyx. For some procedures in which the distal end/tip of the ureteroscope is used as the percutaneous access target, it may be desirable for the distal tip of the ureteroscope to be as close as possible to the papilla/calyx interface during percutaneous access/approximation.

The terms "scope" and "endoscope" are used herein according to their broad and ordinary meanings, and may refer to any type of elongate medical instrument having image generating, viewing, and/or capturing functionality and configured to be introduced into any type of organ, cavity, lumen, chamber, or space of a body. For example, references herein to scopes or endoscopes may refer to a ureteroscope, cystoscope, nephroscope, bronchoscope, arthroscope, colonoscope, laparoscope, borescope, or the like. Scopes/endoscopes, in some instances, may comprise a rigid or flexible tube, and may be dimensioned to be passed within an outer sheath, catheter, introducer, or other lumentype device, or may be used without such devices.

Robotic-assisted percutaneous procedures can be implemented in connection with various medical procedures, such as kidney stone removal procedures, wherein robotic tools can enable a physician/urologist to perform endoscopic target access (e.g., ureteroscope) as well as percutaneous access or/treatment. However, movements of target anatomical features during operation can be problematic in cases where the operating physician relies on a fixed percutaneous access target position. Advantageously, aspects of the present disclosure relate to real-time target tracking/guidance in medical procedures, which may be utilized by the operating physician to direct a percutaneous-access instrument (e.g., needle or other rigid tool) and/or to guide robotic instrumentation, such as by adjusting endoscope position and/or alignment automatically in response to such real-time target-tracking information. To facilitate such functionality, embodiments of the present disclosure may advantageously provide mechanisms for automatic target detection, tracking, and/or three-dimensional positioned estimation to assist physicians (e.g., urologists) to achieve relatively efficient and accurate percutaneous access for various surgical operations, such as nephroscopy. Although aspects of the present disclosure are described herein for convenience in the context of ureteroscope-guided nephroscopy, it should be understood that inventive aspects of the present disclosure may be implemented in any suitable or desirable type of percutaneous and/or endoscopic medical procedure, whether robotic or not.

Medical System

FIG. 1 illustrates an example medical system 10 for performing various medical procedures in accordance with aspects of the present disclosure. The medical system 10 includes a robotic system 11 configured to engage with and/or control a medical instrument 32 to perform a procedure on a patient 13. The medical system 10 also includes a control system 50 configured to interface with the robotic system 11, provide information regarding the procedure, and/or perform a variety of other operations. For example, the control system 50 can include a display 42 to present certain information to assist the physician 5. The medical system 10 can include a table 15 configured to hold the patient 130. The system 10 may further include an electromagnetic (EM) field generator (not shown; see FIG. 3), which may be held by one or more of the robotic arms 12 of the robotic system 11, or may be a stand-alone device.

In some implementations, the system 10 may be used to perform a percutaneous procedure, such as percutaneous nephrolithotomy (PCNL). To illustrate, if the patient 13 has a kidney stone 80 that is too large to be removed through the urinary tract, the physician can perform a procedure to remove the kidney stone through a percutaneous access point on the patient 13. In some embodiments, the physician can interact with the control system 50 and/or the robotic system 11 to control the robotic system 11 to advance and navigate the medical instrument 32 (e.g., a scope) from the urethra 67, through the bladder 65, up the ureter 63, and into the kidney 70 where the stone 80 is located. The control system 50 can provide information via the display 42 regarding the medical instrument 32, such as real-time endoscopic images captured therewith, to assist the physician 5 in navigating the medical instrument.

The renal anatomy is described here for reference with respect to certain medical procedures relating to aspects of the present inventive concepts. The kidneys, shown roughly in typical anatomical position in FIG. 1, generally comprise two bean-shaped organs located on the left and right in the retroperitoneal space. In adult humans, the kidneys are generally about 11 cm in length. The kidneys receive blood from the paired renal arteries; blood exits into the paired renal veins, neither of which is shown for visual clarity. Each kidney 70 is attached to a ureter 63, which is a tube that carries excreted urine from the kidney to the bladder 65.

The kidneys are typically located relatively high in the abdominal cavity and lie in a retroperitoneal position at a slightly oblique angle. The asymmetry within the abdominal cavity, caused by the position of the liver, typically results in the right kidney being slightly lower and smaller than the left, and being placed slightly more to the middle than the left kidney. On top of each kidney is an adrenal gland. The upper parts of the kidneys are partially protected by the 11th and 12th ribs. Each kidney, with its adrenal gland is surrounded by two layers of fat: the perirenal fat present between renal fascia and renal capsule and pararenal fat superior to the renal fascia.

The kidney participates in the control of the volume of various body fluid compartments, fluid osmolality, acid-base balance, various electrolyte concentrations, and removal of toxins. The kidneys provide filtration functionality by secreting certain substances and reabsorbing others. Examples of substances secreted into the urine are hydrogen, ammonium, potassium and uric acid. In addition, the kidneys also carry out various other functions, such as hormone synthesis, and others.

A recessed area on the concave border of the kidney 70 is the renal hilum 78, where the renal artery (not shown) enters the kidney and the renal vein (not shown) and ureter 63 leave. The kidney is surrounded by tough fibrous tissue, the renal capsule 74, which is itself surrounded by perirenal fat, renal fascia, and pararenal fat. The anterior (front) surface of these tissues is the peritoneum, while the posterior (rear) surface is the transversalis fascia.

The functional substance, or parenchyma, of the kidney is divided into two major structures: the outer renal cortex 77 and the inner renal medulla 87. These structures take the shape of a plurality of cone-shaped renal lobes, each containing renal cortex surrounding a portion of medulla called a renal pyramid 72. Between the renal pyramids 72 are projections of cortex called renal columns 73. Nephrons (not shown in detail in FIG. 1), the urine-producing functional structures of the kidney, span the cortex and medulla. The initial filtering portion of a nephron is the renal corpuscle, which is located in the cortex. This is followed by a renal tubule that passes from the cortex deep into the medullary pyramids. Part of the renal cortex, a medullary ray is a collection of renal tubules that drain into a single collecting duct.

The tip, or papilla 79, of each pyramid empties urine into a respective minor calyx 75; minor calyces 75 empty into major calyces 76, and major calyces 76 empty into the renal pelvis 71, which transitions to the ureter 63. At the hilum 78, the ureter 63 and renal vein exit the kidney and the renal artery enters. Hilar fat and lymphatic tissue with lymph nodes surrounds these structures. The hilar fat is contiguous with a fat-filled cavity called the renal sinus. The renal sinus collectively contains the renal pelvis and calyces and separates these structures from the renal medullary tissue.

With further reference to the medical system 10, the medical instrument (e.g., scope) 32 can be advanced into the kidney 70 through the urinary tract. Once at the site of the kidney stone 80 (e.g., within a calyx of the kidney 70 through which the stone 80 is accessible), the medical instrument 32 can be used to designate/tag a target location for percutaneous access to the kidney 70. To minimize damage to the kidney and/or surrounding anatomy, the physician 5 can designate a particular papilla 79 of the kidney 70 as the target location for entering into the kidney with a percutaneous-access instrument (e.g., needle; not shown). However, other target locations can be designated or determined. Once the percutaneous-access instrument has reached the target location (e.g., calyx), the utilized percutaneous access path may be used to extract the kidney stone 80 from the patient 13.

In the example of FIG. 1, the medical instrument 32 is implemented as a scope. However, the medical instrument 32 can each be implemented as any suitable type of medical instrument, such as a catheter, a guidewire, a lithotripter, a basket retrieval device, and so on. In some embodiments, a medical instrument is a steerable device, while other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments.

A scope, such as the scope 32, can be configured to navigate within the human anatomy, such as within a natural orifice or lumen of the human anatomy. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), and so on.

The robotic system 11 can be configured to at least partly facilitate execution of a medical procedure. The robotic system 11 can be arranged in a variety of ways depending on the particular procedure. The robotic system 11 can include one or more robotic arms 12 configured to engage with and/or control the scope 32 to perform a procedure. As shown, each robotic arm 12 can include multiple arm segments coupled to joints, which can provide multiple degrees of movement. In the example of FIG. 1, the robotic system 110 is positioned proximate to the patient's legs and the robotic arms 12 are actuated to engage with and position the scope 32 for access into an access point, such as the urethra 67 of the patient 13. When the robotic system 110 is properly positioned, the scope 120 can be inserted into the patient 13 robotically using the robotic arms 12, manually by the physician 5, or a combination thereof.

Figure 2:
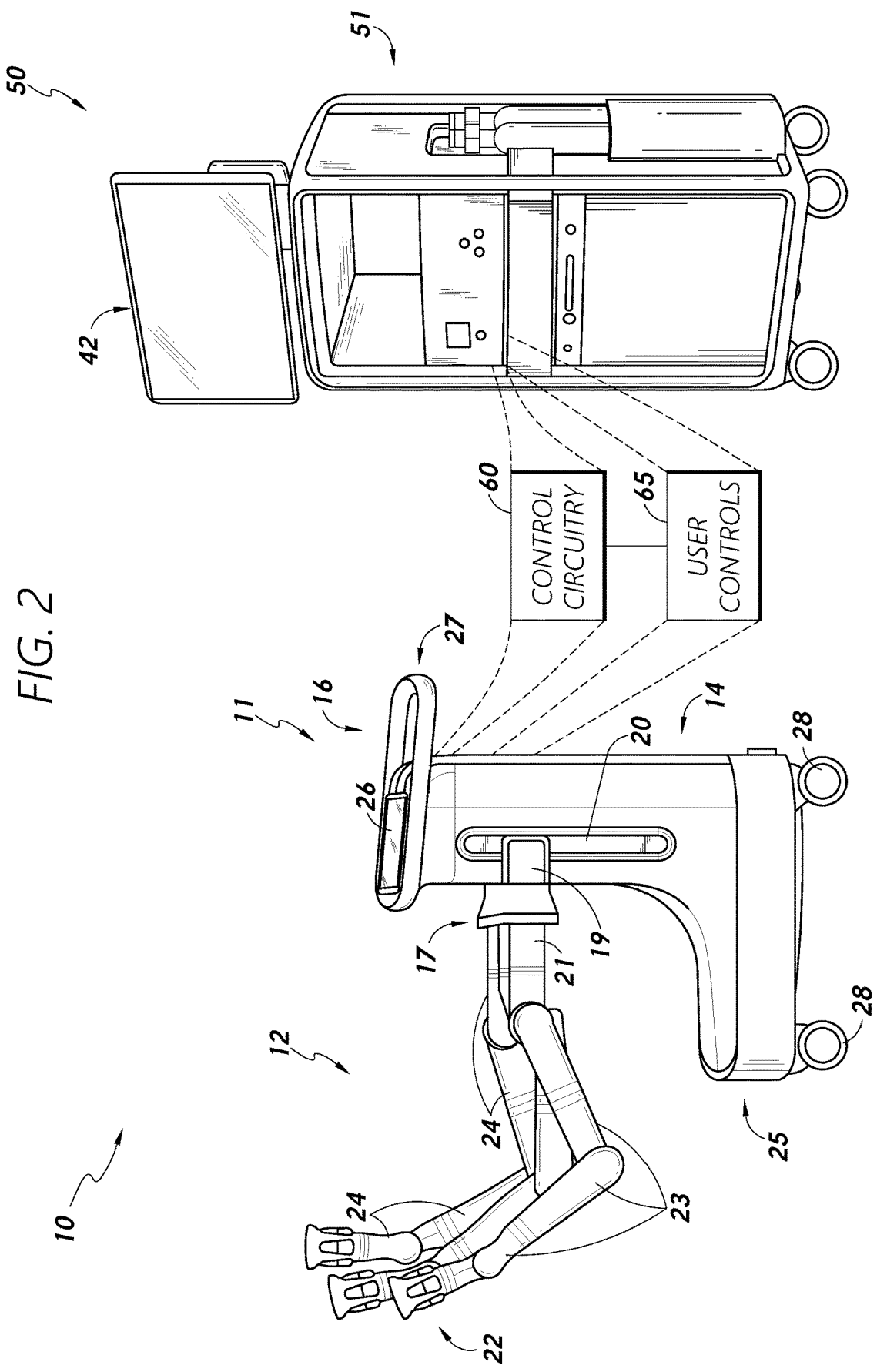
FIG. 2 illustrates example devices that may be implemented in the medical system of FIG. 1 in accordance with one or more embodiments.
Figure 3:
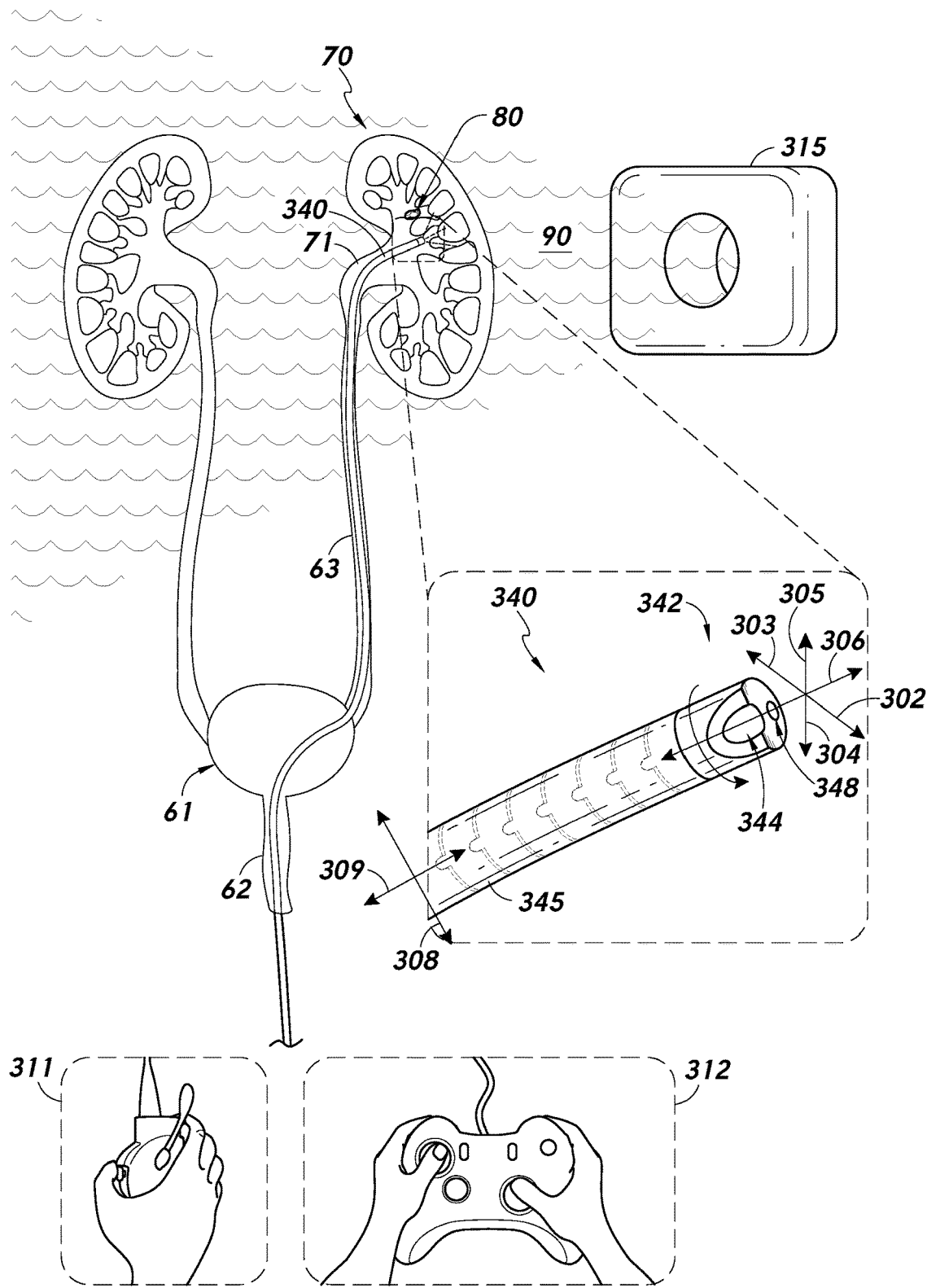
FIG. 3 illustrates a ureteroscope disposed portions of the urinary system in accordance with one or more embodiments.

The robotic system 11 can be coupled to any component of the medical system 100, such as the control system 50, the table 15, the EM field generator (not shown; see FIG. 3), the scope 32, and/or a percutaneous-access instrument (e.g., needle; see FIG. 3). In some embodiments, the robotic system 11 is communicatively coupled to the control system 50. For example, the robotic system 11 may be configured to receive a control signal from the control system 50 to perform an operation, such as to position a robotic arm 12 in a particular manner, manipulate the scope 32, and so on. In response, the robotic system 11 can control a component of the robotic system 11 to perform the operation. In some embodiments, the robotic system 11 is configured to receive images and/or image data from the scope 32 representing internal anatomy of the patient 13, namely the urinary system with respect to the particular depiction of FIG. 1, and/or send images/image data to the control system 50 (which can then be displayed on the display 43 or other output device). Furthermore, in some embodiments, the robotic system 11 is coupled to a component of the medical system 10, such as the control system 50, in such a manner as to allow for fluids, optics, power, or the like to be received therefrom. Additional example details of a robotic system are discussed in further detail below in reference to FIG. 2.

The control system 50 can be configured to provide various functionality to assist in performing a medical procedure. In some embodiments, the control system 50 can be coupled to the robotic system 11 and operate in cooperation with the robotic system 11 to perform a medical procedure on the patient 13. For example, the control system 50 can communicate with the robotic system 11 via a wireless or wired connection (e.g., to control the robotic system 11 and/or the scope 32, receive images captured by the scope 32, etc.), provide fluids to the robotic system 11 via one or more fluid channels, provide power to the robotic system 11 via one or more electrical connections, provide optics to the robotic system 11 via one or more optical fibers or other components, and so on. Further, in some embodiments, the control system 50 can communicate with a needle and/or nephroscope to receive position data therefrom. Moreover, in some embodiments, the control system 50 can communicate with the table 15 to position the table 15 in a particular orientation or otherwise control the table 15. Further, in some embodiments, the control system 50 can communicate with the EM field generator (not shown) to control generation of an EM field in an area around the patient 13.

The control system 50 can include various I/O devices configured to assist the physician 5 or others in performing a medical procedure. For example, the control system 50 can include certain input/output (I/O) components configured to allow for user input to control the scope 32, such as to navigate the scope 32 within the patient 13. In some embodiments, example, the physician 5 can provide input to the control system and/or robotic system, wherein in response, control signals can be sent to the robotic system 11 to manipulate the scope 32. As also shown in FIG. 1, the control system 50 can include the display 42 to provide various information regarding a procedure. For example, the display 42 can provide information regarding the scope 32. For example, the control system 50 can receive real-time images that are captured by the scope 32 and display the real-time images via the display 42. Additionally or alternatively, the control system 140 can receive signals (e.g., analog, digital, electrical, acoustic/sonic, pneumatic, tactile, hydraulic, etc.) from a medical monitor and/or a sensor associated with the patient 13, and the display 42 can present information regarding the health or environment of the patient 13. Such information can include information that is displayed via a medical monitor including, for example, a heart rate (e.g., ECG, I-IRV, etc.), blood pressure/rate, muscle bio-signals (e.g., EMG), body temperature, blood oxygen saturation (e.g., $SpO_2$), $CO_2$, brainwaves (e.g., EEG), environmental and/or local or core body temperature, and so on.

To facilitate the functionality of the control system 50, the control system can include various components (sometimes referred to as "subsystems"). For example, the control system 50 can include control electronics/circuitry, as well as one or more power sources, pneumatic devices, optical sources, actuators, data storage devices, and/or communication interfaces. In some embodiments, the control system 50 includes control circuitry comprising a computer-based control system that is configured to store executable instructions, that when executed, cause various operations to be implemented. In some embodiments, the control system 50 is movable, while in other embodiments, the control system 50 is a substantially stationary system. Although various functionality and components are discussed as being implemented by the control system 50, any of such functionality and/or components can be integrated into and/or performed by other systems and/or devices, such as the robotic system 11, the table 15, for example. Components of an example robotic system are discussed in further detail below in reference to FIG. 2.

The medical system 10 can provide a variety of benefits, such as providing guidance to assist a physician in performing a procedure (e.g., instrument tracking, instrument alignment information, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. For example, the medical system 10 can provide guidance information to assist a physician in using various medical instruments to access a target anatomical feature while minimizing bleeding and/or damage to anatomy (e.g., critical organs, blood vessels, etc.). Further, the medical system 10 can provide non-radiation-based navigational and/or localization techniques to reduce physician and patient exposure to radiation and/or reduce the amount of equipment in the operating room. Moreover, the medical system 10 can provide functionality that is distributed between at least the control system 50 and the robotic system 11, which may be independently movable. Such distribution of functionality and/or mobility can enable the control system 50 and/or the robotic system 11 to be placed at locations that are optimal for a particular medical procedure, which can maximize working area around the patient, and/or provide an optimized location for a physician to perform a procedure.

The various components of the system 10 can be communicatively coupled to each other over a network, which can include a wireless and/or wired network. Example networks include one or more personal area networks (PANs), local area networks (LANs), wide area networks (WANs), Internet area networks (IANs), cellular networks, the Internet, etc. Furthermore, in some embodiments, the various components of the system 10 can be connected for data communication, fluid/gas exchange, power exchange, and so on via one or more support cables, tubes, or the like.

FIG. 2 provides a detailed illustration of embodiments of the robotic system 11 (e.g., cart-based robotically-enabled system) and the control system 50 shown in FIG. 1. The robotic system 11 generally includes an elongated support structure 14 (also referred to as a "column"), a robotic system base 25, and a console 16 at the top of the column 14. The column 14 may include one or more arm supports 17 (also referred to as a "carriage") for supporting the deployment of one or more robotic arms 12 (three shown in FIG. 2). The arm support 17 may include individually-configurable arm mounts that rotate along a perpendicular axis to adjust the base of the robotic arms 12 for better positioning relative to the patient. The arm support 17 also includes a column interface 19 that allows the arm support 17 to vertically translate along the column 14.

The column interface 19 can be connected to the column 14 through slots, such as slot 20, that are positioned on opposite sides of the column 14 to guide the vertical translation of the arm support 17. The slot 20 contains a vertical translation interface to position and hold the arm support 17 at various vertical heights relative to the robotic system base 25. Vertical translation of the arm support 17 allows the robotic system 11 to adjust the reach of the robotic arms 12 to meet a variety of table heights, patient sizes, and physician preferences. Similarly, the individually-configurable arm mounts on the arm support 17 allow the robotic arm base 21 of robotic arms 12 to be angled in a variety of configurations.

The robotic arms 12 may generally comprise robotic arm bases 21 and end effectors 22, separated by a series of linkages 23 that are connected by a series of joints 24, each joint comprising one or more independent actuators. Each actuator may comprise an independently-controllable motor. Each independently-controllable joint 24 can provide or represent an independent degree of freedom available to the robotic arm. In some embodiments, each of the arms 12 has seven joints, and thus provides seven degrees of freedom, including "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The robotic system base 25 balances the weight of the column 14, arm support 17, and arms 12 over the floor. Accordingly, the robotic system base 25 may house heavier components, such as electronics, motors, power supply, as well as components that selectively enable movement or immobilize the robotic system. For example, the robotic system base 25 includes wheel-shaped casters 28 that allow for the robotic system to easily move around the room prior to a procedure. After reaching the appropriate position, the casters 28 may be immobilized using wheel locks to hold the robotic system 11 in place during the procedure.

Positioned at the upper end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite arm support 17. From this position, the physician may view the console 16, robotic arms 12, and patient while operating the console 16 from behind the robotic system 11. As shown, the console 16 can also include a handle 27 to assist with maneuvering and stabilizing robotic system 11.

The end effector 22 of each of the robotic arms 12 may comprise an instrument device manipulator (IDM), which may be attached using a mechanism changer interface (MCI). In some embodiments, the IDM can be removed and replaced with a different type of IDM, for example, a first type of IDM may manipulate an endoscope, while a second type of IDM may manipulate a laparoscope. The MCI can include connectors to transfer pneumatic pressure, electrical power, electrical signals, and/or optical signals from the robotic arm 12 to the IDM. The IDMs may be configured to manipulate medical instruments (e.g., surgical tools/instruments), such as the scope 32 using techniques including, for example, direct drive, harmonic drive, geared drives, belts and pulleys, magnetic drives, and the like.

The control system 50 shown in FIG. 2 may serve as a command console for the example surgical robotic system 11. The control system 50 can include a console base 51 and one or more display devices 42.

The system 10 may include certain control circuitry 60 configured to perform certain of the functionality described herein. The control circuitry 60 may be part of the robotic system, the control system 50, or both. That is, references herein to control circuitry may refer to circuitry embodied in a robotic system, a control system, or any other component of a medical system, such as the medical system 10 shown in FIG. 1. The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry referenced herein may further include one or more circuit substrates (e.g., printed circuit boards), conductive traces and vias, and/or mounting pads, connectors, and/or components. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

With further reference to FIG. 2, the control circuitry 60 may comprise a computer-readable medium storing hard-coded and/or operational instructions corresponding to at least some of the steps and/or functions illustrated in one or more of the present figures and/or described herein. Such computer-readable medium can be included in an article of manufacture in some instances. The control circuitry 60 may be entirely locally maintained/disposed or may be remotely located at least in part (e.g., communicatively coupled indirectly via a local area network and/or a wide area network).

In some embodiments, at least a portion of the control circuitry 60 is integrated with the robotic system 11 (e.g., in the base 25, column 14, and/or console 14) or another system communicatively coupled to the robotic system 11. In some embodiments, at least a portion of the control circuitry 60 is integrated with the control system 50 (e.g., in the console base 51 and/or display unit 42). Therefore, any description of functional control circuitry herein may be understood to be embodied in either the robotic system 11, the control system 50, or both, and/or at least in part in one or more other local or remote systems/devices.

The system 10 further includes certain user controls 65, which may comprise any type of user input (and/or output) devices or device interfaces, such as one or more buttons, keys, joysticks, handheld controllers (e.g., video-game-type controllers), computer mice, trackpads, trackballs, control pads, and/or sensors (e.g., motion sensors or cameras) that capture hand gestures and finger gestures, and/or interfaces/connectors therefore. The user controls 65 are communicatively and/or physically coupled to at least some of the control circuitry 60.

In some embodiments, the user controls 65 and/or control circuitry 60 are configured to receive user input to allow a user to control a medical instrument, such as an endoscope or nephroscope, such as an instrument manipulatable at least in part by a robotic system, in a velocity mode or position control mode. In velocity mode, the user may be permitted to directly control pitch and yaw motion of a distal end of, for example, an endoscope or other instrument based on direct manual control using the controls 65. For example, movement on a joystick may be mapped to yaw and pitch movement in the distal end of the scope/device. In some embodiments, the user controls 65 are configured to provide haptic feedback to the user. For example, a joystick or other control mechanism may vibrate to indicate an invalid or potentially problematic input. In some embodiments, the control system 50 and/or robotic system 11 can also provide visual feedback (e.g., pop-up messages) and/or audio feedback (e.g., beeping) to indicate issues associated with robotic operation.

In position control mode, the control circuitry 60 may use a three-dimensional (3D) map of a patient and/or pre-determined computer models of the patient to control a medical instrument (e.g., endoscope). For example, the control circuitry 60 can be configured to provide control signals to the robotic arms 12 of the robotic system 11 to manipulate the relevant instrument to position the same at a target location, position, and/or orientation/alignment. For embodiments implementing 3D mapping, position control mode may require sufficiently accurate mapping of the anatomy of the patient.

In some embodiments, a user can manually manipulate a robotic arm 12 of the robotic system 11 without using the user controls 65. For example, during setup in a surgical operating room, a user may move the robotic arms 12 and/or any other medical instruments to provide desired access to a patient. The robotic system 11 may rely on force feedback and inertia control from the user to determine appropriate configuration of the robotic arms 12 and associated instrumentation.

The display device(s) 42 of the control system 50 may be integrated with the user controls 65, for example, as a tablet device with a touchscreen providing for user input. The display device(s) 42 can be configured to provide data and input commands to the robotic system 11 using integrated display touch controls. The display device(s) 42 can be configured to display graphical user interfaces showing information about the position and orientation of various instruments operating within the patient and/or system based on information provided by one or more position sensors. In some embodiments, position sensors associated with medical instruments (e.g., an endoscope) may be configured to generate signals indicative of position and transmit the same on wires and/or transmitters coupled to the sensors. Such connectivity components may be configured to transmit the position information to the console base 51 for processing thereof by the control circuitry 60 and for presentation via the display device(s).

FIG. 3 illustrates a ureteroscope 340 disposed in portions of the urinary system of a patient in accordance with one or more embodiments of the present disclosure. As referenced above, ureteroscope procedures can be implemented for investigating abnormalities in human ureters and/or treating the same. For example, ureteroscope procedures can be implemented to treat and/or remove kidney stones. Such procedures may be implemented manually at least in part and/or may be performed using robotic technologies at least in part, such as the robotic system 11 shown in FIGS. 1 and 2. For example, use of robotic devices and/or systems for certain endoscopic procedures can provide relatively higher precision, control, and/or coordination compared to strictly manual procedures. In some embodiments, the scope 340 includes a working channel 344 for deploying medical instruments (e.g., lithotripters, basketing devices, forceps, etc.), irrigation, and/or aspiration to an operative region at a distal end of the scope.

The scope 340 can be articulable, such as with respect to at least a distal portion of the scope, so that the scope can be steered within the human anatomy. In some embodiments, the scope 340 is configured to be articulated with, for example, five degrees of freedom, including XYZ coordinate movement, as well as pitch and yaw. In some embodiments, the needle sensor provides six degrees of freedom, including X, Y, and Z ordinate positions, as well as pitch, law, and yaw. Position sensor(s) of the scope 340 may likewise have similar degrees of freedom with respect to the position information they produce/provide. Figure illustrates multiple degrees of motion of the scope 340 according to some embodiments. As shown in FIG. 3, the tip 342 of the scope 340 can be oriented with zero deflection relative to a longitudinal axis 306 thereof (also referred to as a "roll axis").

To capture images at different orientations of the tip 342, a robotic system may be configured to deflect the tip 342 on a positive yaw axis 302, negative yaw axis 303, positive pitch axis 304, negative pitch axis 305, or roll axis 306. The tip 342 or body 345 of the scope 342 may be elongated or translated in the longitudinal axis 306, x-axis 308, or y-axis 309. The scope 340 may include a reference structure (not shown) to calibrate the position of the scope. For example, a robotic system may measure deflection of the scope 340 relative to the reference structure. The reference structure can be located, for example, on a proximal end of the endoscope 340 and may include a key, slot, or flange. The reference structure can be coupled to a first drive mechanism for initial calibration and coupled to a second drive mechanism to perform a surgical procedure.

For robotic implementations, robotic arms of a robotic system can be configured/configurable to manipulate the scope 340 using elongate movement members. The elongate movement members may include one or more pull wires (e.g., pull or push wires), cables, fibers, and/or flexible shafts. For example, the robotic arms may be configured to actuate multiple pull wires (not shown) coupled to the scope 340 to deflect the tip 342 of the scope 118. Pull wires may include any suitable or desirable materials, such as metallic and non-metallic materials such as stainless steel, Kevlar, tungsten, carbon fiber, and the like. In some embodiments, the scope 340 is configured to exhibit nonlinear behavior in response to forces applied by the elongate movement members. The nonlinear behavior may be based on stiffness and compressibility of the scope, as well as variability in slack or stiffness between different elongate movement members.

The scope (e.g., endoscope/ureteroscope) 340 may comprise a tubular and flexible medical instrument that is configured to be inserted into the anatomy of a patient to capture images of the anatomy. In some embodiments, the scope 340 can accommodate wires and/or optical fibers to transfer signals to/from an optical assembly and a distal end 342 of the scope 340, which can include an imaging device 348, such as an optical camera.

The camera/imaging device 348 can be used to capture images of an internal anatomical space, such as a target calyx/papilla of the kidney 70. The scope 340 may further be configured to accommodate optical fibers to carry light from proximately-located light sources, such as light-emitting diodes, to the distal end 342 of the scope. The distal end 342 of the scope 340 can include ports for light sources to illuminate an anatomical space when using the camera/imaging device. In some embodiments, the scope 340 is configured to be controlled by a robotic system similar in one or more respects to the robotic system 11 shown in FIGS. 1 and 2. The imaging device may comprise an optical fiber, fiber array, and/or lens. The optical components move along with the tip of the scope 340 such that movement of the tip of the scope results in changes to the images captured by the imaging device(s) 348.

For percutaneous nephrolithotomy (PCNL) procedure, access is made into the target calyx through the skin and intervening tissue of the patient. Generally, the preferred access to the calyces of the kidney is through the soft-tissue papilla structures, wherein access through such tissue may be generally associated with reduced risks of bleeding and/or other complications. Where a needle is inserted through a papilla structure, in addition to freedom from bleeding, such pathway can provide full access to the interconnected internal channels (e.g., calyces) of the kidney.

Although PCNL represents a relatively effective method for treating large renal calculi, many physicians choose other procedures due in part to the difficulty of accurately targeting the target papilla/calyx. More particularly, performing a PCNL involves using a needle to gain percutaneous access to a target calyx of the kidney through a patient's flank. This step can be considered extremely important to the ultimate success of the procedure because the physician must select a needle path to the kidney that does not traverse surrounding organs and also allows for a rigid instrument to reach and treat the urinary stone. If the physician fails to do so effectively, they risk causing a visceral or pleural injury or not being able to completely treat the stone. Due to these challenges, the learning curve associated with gaining percutaneous needle access to perform a PCNL a suitable patient position (e.g., the modified supine position) is very high.

In some procedures, the physician(s) study a patient's preoperative computed tomography (CT) images to determine the location of the urinary stone, the location of surrounding organs and bony structures, and examine the morphometry of the calyces. With this knowledge, the physician(s) may mentally generate a pre-operative plan for the percutaneous needle path. Typically, physicians must identify a posterior calyx to puncture to accommodate a rigid instrument. Specifically, a posterior calyx generally provides a relatively straight shot into the renal pelvis. Physicians must try to insert the needle into the kidney through the papilla to avoid damaging renal vasculature and cause bleeding. Intraoperatively, physicians in some procedures rely on fluoroscopy or ultrasound to guide the alignment and insertion of the needle to the target calyx. However, the resolution and interpretation difficulty associated with such imaging techniques can result in a relatively high degree of difficulty in satisfactorily executing the needle puncture. Therefore, embodiments of the present disclosure that provide improved tracking and visualization of target anatomical features, such as papillae and calyces, can improve operational results and appeal to a larger subset of physicians than other PCNL methodologies.

In some embodiments, the medical instrument (e.g., scope) 340 includes a sensor that is configured to generate and/or send sensor position data to another device. The sensor position data can indicate a position and/or orientation of the medical instrument 340 (e.g., the distal end 342 thereof) and/or can be used to determine/infer a position/orientation of the medical instrument. For example, a sensor (sometimes referred to as a "position sensor") can include an electromagnetic (EM) sensor with a coil of conductive material, or other form/embodiment of an antenna.

FIG. 3 shows an EM field generator 315, which is configured to broadcast an EM field 90 that is detected by the EM sensor on the medical instrument. The magnetic field 90 can induce small currents in coils of the EM position sensor, which may be analyzed to determine a distance and/or angle/orientation between the EM sensor and the EM field generator 315. Further, the medical instrument/scope 340 can include other types of sensors, such as a shape sensing fiber, accelerometer(s), gyroscope(s), satellite-based positioning sensor(s) (e.g., global positioning system (GPS) sensors), radio-frequency transceiver(s), and so on. In some embodiments, a sensor on a medical instrument can provide sensor data to a control system, which is then used to determine a position and/or an orientation of the medical instrument. In some embodiments, the position sensor is positioned on the distal end 342 of the medical instrument 340, while in other embodiments the sensor is positioned at another location on the medical instrument. the ureteroscope may be driven to a position in proximity to the target papilla.

In some implementations, as described in further detail below, the distal end of the ureteroscope 340 may be advanced to contact the target anatomical feature (e.g., papilla). With the position sensor associated with the distal end of the scope 340 in contact and/or proximity to the target anatomical feature, the position of the distal end of the scope 340 may be recorded as the target percutaneous access position to which the percutaneous-access instrument (e.g., needle) may be directed to access target calyx through the papilla.

Certain embodiments of the present disclosure advantageously help to automate and guide physicians through the process for gaining percutaneous to target anatomical features. For example, electromagnetic positioning and scope images can be used together to guide the insertion of a needle into a patient. Such solutions can allow non-expert physicians to gain access into the kidney in, for example, the modified supine position and to be able to perform PCNL.

Certain embodiments of the present disclosure involve position-sensor-guided percutaneous access to a target treatment site, such as a target location in the kidney. For example, where the scope 340 is fitted with one or more electromagnetic sensors, and the nephroscope access needle further includes one or more electromagnetic sensors, and such sensors are subjected to the electromagnetic field 90 created by the field generator 315, associated system control circuitry can be configured to detect and track their locations. In some embodiments, the tip of the ureteroscope 340 acts as a guiding beacon while the user inserts the percutaneous access needle. Such solutions can allow the user to hit the target from a variety of approaches, thereby obviating the need to rely on fluoroscopic or ultrasound imaging modalities.

In some embodiments, a control system (not shown in FIG. 3) associated with the scope 340 is configured to implement localization/positioning techniques to determine and/or track a location/position of a medical instrument, such as the scope 340 and/or percutaneous access needle (not shown). In some examples, as noted above, the EM field generator 315 is configured to provide an EM field 90 within the environment of the patient. The scope 340 and/or the percutaneous access needle can include an EM sensor that is configured to detect EM signals and send sensor data regarding the detected EM signals to the control system. The control system can analyze the sensor data to determine a position and/or orientation of the scope 340 (e.g., a distance and/or angle/orientation between the EM sensor and the EM field generator 315). Alternatively or additionally, in some examples, the control system can use other techniques to determine a position and/or an orientation of the scope 340. For instance, the scope 340 (and/or needle) can include a shape-sensing fiber, an accelerometer, a gyroscope, an accelerometer, a satellite-based positioning sensor (e.g., a global positioning system (GPS)), a radio-frequency transceiver, and so on. The control system can receive sensor data from the scope 340 and determine a position and/or an orientation thereof. In some embodiments, the control system can track a position and/or an orientation of the scope 340 in real-time with respect to a coordinate system and/or the anatomy of the patient.

The scope 340 may be controllable in any suitable or desirable way, either based on user input or automatically. The controls 311, 312 provide examples that may be used to receive user input. In some embodiments, the controls of the scope 340 are located on a proximal handle of the scope, which may be relatively difficult to grasp in some procedural postures/positions as the orientation of the ureteroscope changes. In some embodiments, the scope 340 is controlled using a two-handed controller, as in image 312. Although the controllers 311, 312 are shown as hand-held controllers, user input may be received using any type of I/O device, such as a touchscreen/pad, a mouse, a keyboard, a microphone, etc.

Figure 4:
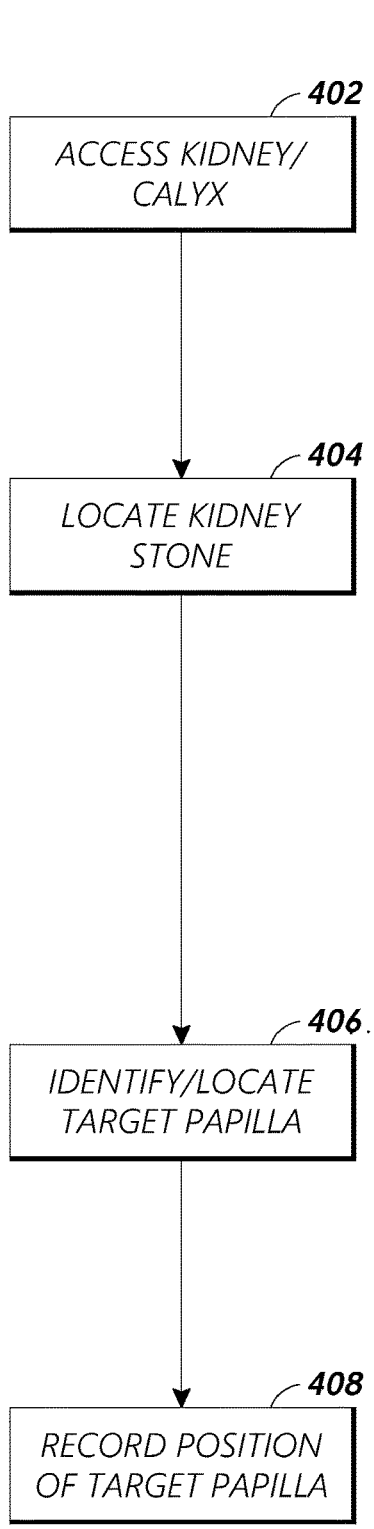
Figure 1:
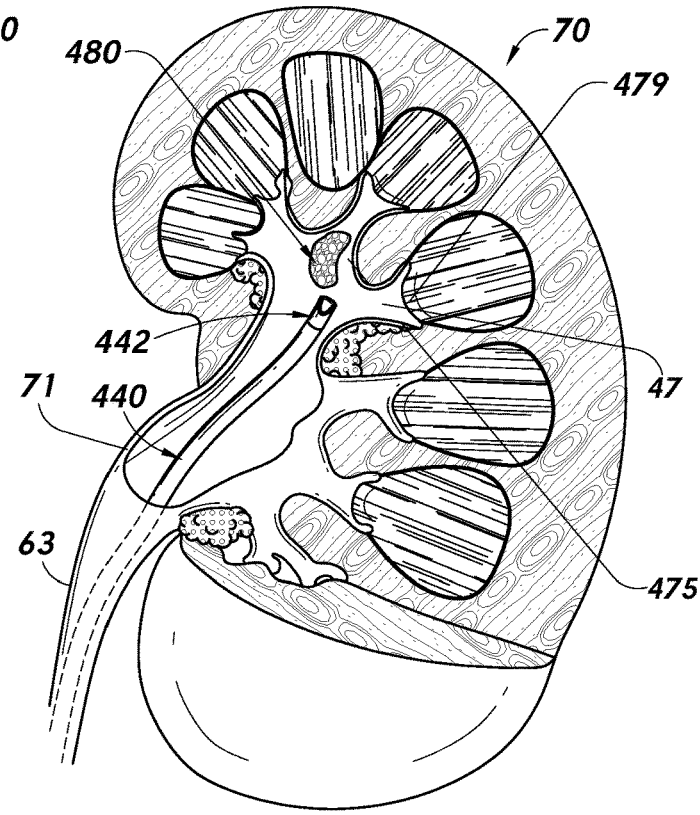
Figure 5:
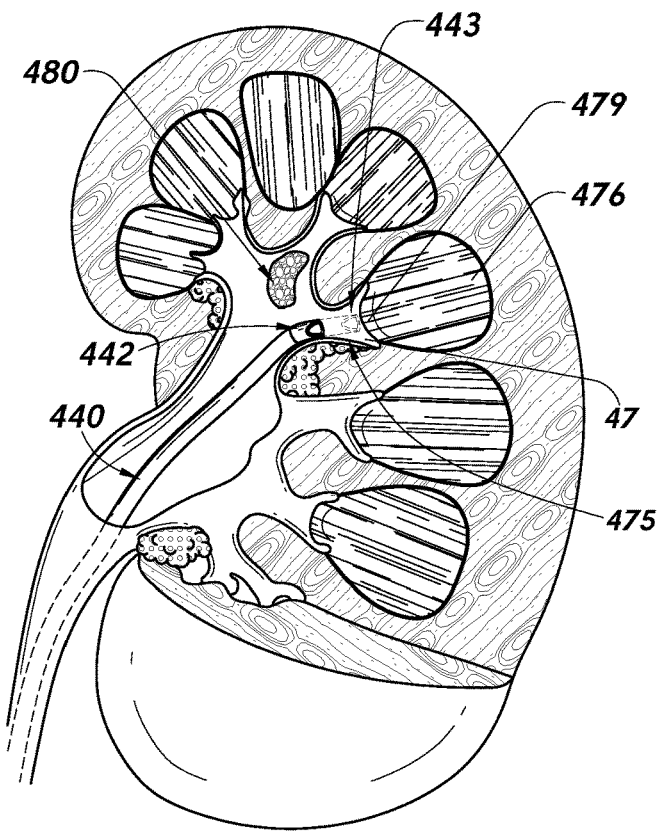

FIG. 4 (represented in parts 4-1 and 4-2) is a flow diagram illustrating a process 400 for accessing a target calyx or other organ of a patient in accordance with one or more embodiments of the present disclosure. FIG. 5 (represented in parts 5-1 and 5-2) shows certain images corresponding to various blocks, states, and/or operations associated with the process of FIG. 4 in accordance with one or more embodiments. The process 400 may involve percutaneous access to the kidney 70 for kidney stone removal (e.g., PCNL). Such percutaneous access may be desirable for extraction of stones that are sufficiently large that removal via ureteroscope is impractical or undesirable. For example, stones can be greater than 2 cm in diameter, whereas certain ureteroscopes have a working channel through which a stone or fragment can be removed that has a diameter of about 1.2 mm. Although breaking stones into smaller fragments for removal via ureteroscopy does work in many instances, studies have shown that leftover stone debris is often the source of new stone formation, necessitating future similar treatments.

At block 402, the process 400 involves accessing the kidney through the ureter of the patient using a ureteroscope 440, as described above. In particular, the operation of block 402 may involve advancing the scope 440 through the ureter 63, past the renal pelvis 71, and into an area at or near one or more calyces.

At block 404, the process 400 involves locating, using an image-capturing device (e.g. camera) associated with the distal end 442 of the endoscope, a kidney stone 480, for which the patient is to be treated. For example, the kidney stone 480 may be extracted at least in part as an objective of the process 400.

At block 406, the process 400 involves identifying a target papilla 479 that is exposed within a target calyx 475 through which access to the kidney stone 480 may be achieved. Identifying the target papilla 479 may be important for creating a workable tract through which access to the kidney stone 480 can be made via percutaneous access. For example, it may be necessary to determine an angle that is appropriate for access by a relatively rigid nephroscope in such a way as to access a calyx (e.g., minor calyx 475) through which the kidney stone 480 can be reached. In some implementations, it may be desirable or necessary to reach the kidney stone(s) 480 through a posterior calyx in order to provide a sufficiently straight access to the ureteropelvic junction 71. Generally, target minor calyces may be considered relatively small targets. For example, such calyces may be approximately 4-8 mm in diameter. Therefore, precise targeting can be critical in order to effectively extract the kidney stone(s).

The path through which needle/nephroscope access to the target calyx 475 is achieved may advantageously be as straight as possible in order to avoid hitting blood vessels around the renal pyramid 476 associated with the papilla 479 through which the needle/nephroscope may be positioned. Furthermore, the position of various critical anatomy of the patient may necessitate navigation through a constrained window of tissue/anatomy of the patient. For example, the lower pole calyces, below the $12^{th}$ rib, may provide a suitable access to avoid the pulmonary pleura. Furthermore, the access path may advantageously be medial to the posterior axillary line (e.g. approximately 1 cm below and 1 cm medial to the tip of the 12 rib) to avoid the colon and/or paraspinal muscle. In addition, the access path may advantageously avoid coming within close proximity to the rib to avoid the intercostal nerves. Furthermore, by targeting entry in the area of the axial center of the calyx 475, major arteries and/or other blood vessels can be avoided in some instances.

At block 408, the process 400 involves tagging/recording the position of the exposed papilla 479 within the target calyx 479 through which the desired access is to be achieved. For example, position information/data may be represented/identifiable in a three-dimensional space, such as an electromagnetic field space.

In order to record the position of the papilla 179, the scope 440 may be advanced to physically touch/contact the target papilla 479, as shown by the advanced scope tip 443, in connection with which such contact position may be identified and/or otherwise indicated as the target position by the scope 440 and/or operator. In some implementations, an electromagnetic beacon or other sensor device associated with the distal end/tip 442 of the ureteroscope may indicate the target position, thereby registering the target position in the electromagnetic field space. After contacting/touching the papilla 479 and recording the position, the end 442 of the scope may be retracted, and the depth of such retraction measured in some manner. In some implementations, the operator may be informed that the distal end 443 of the scope 440 has contacted the papilla 479 by monitoring the camera images generated thereby, which may generally become obstructed/blacked-out when contact is made.

At block 410, the process 400 involves percutaneously introducing a medical instrument 450, such as a needle, into the patient. For example, such access may be made via the flank of the patients in some implementations. At block 412, the process 400 involves directing the percutaneously advanced medical instrument 450 towards the target position to ultimately traverse the target papilla 479 and access the target calyx 475 therethrough.

In some embodiments, visual confirmation of the entry of the tip of the needle 450 into the target calyx 475 may be provided by the camera of the scope 440. For example, the scope 440 may be backed-off from the target position, as described above, to thereby provide a field of view including the papilla 479 within the calyx 475, such that the tip of the needle 450 may be seen as it protrudes through the surface of the papilla 479.

With the target location recorded, a percutaneously-inserted medical instrument (e.g., the needle 450) may be directed towards the recorded position. However, where such recorded position is static, anatomical motion occurring after recordation of the target position may result in the target position not accurately reflecting the real-time position associated with the target anatomical feature through which access desired. For example, the act of inserting the needle 450 into the patient may cause certain anatomy around the target organ (e.g., the kidney 70) and/or the target organ itself to migrate and/or become distorted/misshaped in some manner, thereby causing the target anatomical feature (e.g., papilla 479) to assume a position/shape different than at the time at which the target access position was recorded. With respect to renal procedures, the ureteroscope 440 may be fixed to the position of the renal pelvis 71, such that deformation and/or motion of the kidney 70 relative to the ureteroscope may result in such target position corruption. Therefore, the papilla 479 may not be accurately tracked once anatomical motion is introduced into the system.

Once needle access has been made to the calyx 475, a larger-diameter device may be exchanged for the needle 450 to provide a larger port for stone removal. In some implementations, the needle 450 comprises a stylet and a cannula. With the needle tip advanced into the calyx 475, the stylet may be removed, leaving the cannula to form an open port to the location of the kidney stone. Through the cannula, a guide wire may be placed and used to perform the remainder of the process to remove the stone 480. for example, the guide wire can be used to pass a deflated balloon or dilator along the wire. The balloon or dilator can be expanded to create a port large enough introduce a hollow suction tube, such as a nephrostomy tube, directly into the calyx 475. At this point, a nephroscope or any one of a number of other instruments may be introduced into the suction tube to assist in removing the stone 480. For example, a stone breaker, laser, ultrasound, basket, grasper, drainage tube, etc. may be used to remove the stone or fragments thereof, and/or drainage tubes, such as nephrostomy catheters, may be deployed down the suction tube to reduce intra-renal pressure. Any combination of such functionality may be embodied in the nephroscope (not shown) and/or the ureteroscope 440.

Image-Processing-Enhanced Instrument Guidance and Automation

The processes described herein, although described in the context of ureteroscope, may apply to any other type of surgical procedure utilizing a position sensor (e.g., electromagnetic field sensor) and/or camera to track a target anatomical feature, such as a papilla or urinary stone. As described, a static position marker may be registered/recorded to identify a target position associated with a target anatomical feature/landmark. In some embodiments, the present disclosure provides systems, devices, and methods for guiding and/or automating endoscope and/or percutaneous-access instruments based at least in part a static position marker in view of certain target-identification and/or target-tracking image-processing techniques. Target identification and tracking in accordance with embodiments of the present disclosure can apply to any type of robotic endoscopy procedure.

In some implementations, certain image data may be collected and used for identifying target anatomical features. Such identification may be achieved at least in part using a machine learning framework. For example, systems, devices, and methods of the present disclosure may provide for identification of target anatomical features in real-time endoscope images, wherein identification of a target anatomical features in an image may prompt certain responsive action. For example, control circuitry communicatively coupled to robotic endoscopy and/or percutaneous-access device(s) may be configured to track movements of a target feature and take action, such as articulating one or more portions of the endoscope (e.g., distal end portion), or adjusting target position data. For example, the control circuitry may be configured to cause the endoscope to articulate so as to center the target position/points at or near a center of the field of view of an interface and/or image field of the endoscope camera.

By utilizing robotic-assisted percutaneous access, a physician may be able to perform operating target access and treatment. Furthermore, percutaneous access can be further assisted utilizing automated target identification and tracking in accordance with aspects of the present disclosure described in greater detail below, which may be relied upon for accurately maintaining the target position for percutaneous access guidance. Percutaneous access guided by scope-enabled target tracking in accordance with aspects of the present disclosure can be relatively less skill-intensive. In some implementations, a single operator or robotic system may carry out the process. Furthermore, the need for fluoroscopy can be obviated.

Automatic Target Detection

Figure 6:
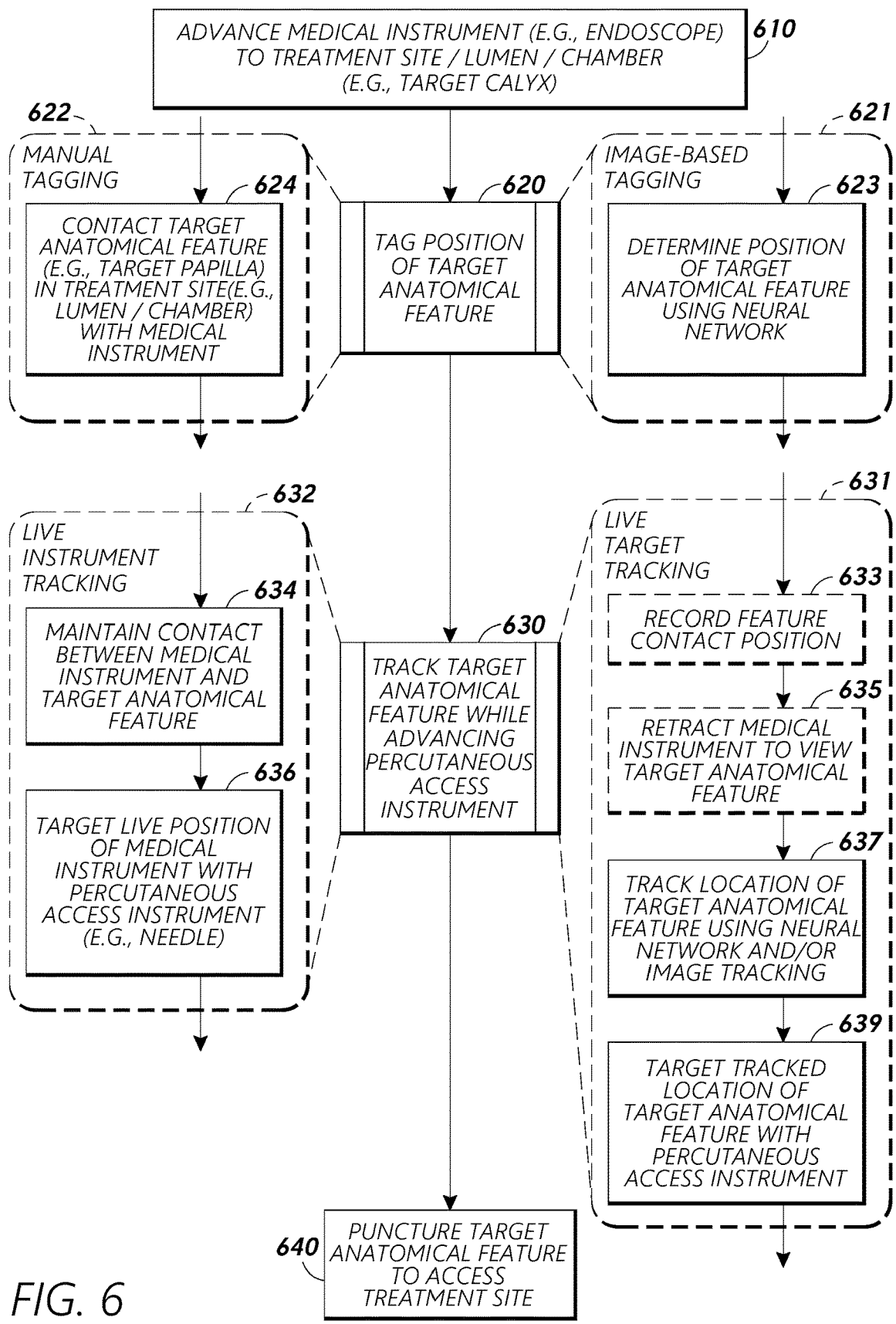
FIG. 6 is a flow diagram illustrating a process for targeting an anatomical feature in accordance with one or more embodiments.

FIG. 6 is a flow diagram illustrating a process 600 for targeting an anatomical feature in accordance with one or more embodiments. Similarly to certain other processes disclosed herein, the process 600 involves, at block 610, advancing a medical instrument, such as a scope (e.g., ureteroscope) to the treatment site, such as lumen or chamber disposed at least partially within a target organ. For example, the operation of block 610 may involve advancing the medical instrument to a target calyx of the kidney of the patient. The relative position between medical instrument and the target may change slightly due to anatomical motion and/or when a percutaneous needle instrument approximates the target in accordance with certain processes disclosed herein. Such relative change on in position can lead to a desire or necessity for tracking the position of the target organ. For example, the position may be tracked in two-dimensional space and the position may be recovered in three-dimensional space, as described in greater detail below.

As referenced above, robotic endoscope-guided percutaneous access in accordance with aspects of the present disclosure can utilize location-tracking technology with respect to the target anatomical feature through which access to the treatment site is achieved. For example, position-tracking mechanisms/sensors associated with the distal end of the medical instruments (e.g., scope) and/or a percutaneous-access instrument (e.g., needle) can be implemented in order to guide the physician/technician in aligning the percutaneous-access instruments with the treatment site (e.g., target calyx). Accurate, real-time target tracking, as enabled by aspects of the present disclosure, can enable relatively precise single-stick access to the treatment site.

At block 620, the process 600 involves tagging a position of the target anatomical. It is better to clarify that, this manual tagging process is not needed when the image processing approach is able to give the 3D location of the target. For example, tagging the position of the target anatomical position can involve determining and/or recording (e.g., capturing in volatile and/or non-volatile data storage of certain control circuitry as shown and described herein). Tagging the position of the target anatomical feature in connection with block 620 can be performed in any suitable or desirable way, such as using an at least partially manual tagging subprocess 622 or an at least partially image-based tagging subprocess 621, which are described below in connection with blocks 624 and 623, respectively.

With respect to certain manual tagging processes, at block 622, the process 600 involves contacting the target anatomical feature in the treatment site with the distal end of the medical instrument. For example, the medical instrument may comprise a sensor device, such as an electromagnetic sensors/beacon that may indicate a position of the distal end of the medical instrument, and therefore, with the distal end of the medical instrument disposed against and/or adjacent to the target anatomical feature, such position reading can be relied upon as indicating the position of the target anatomical feature. As an example, the user may provide input to notify the relevant computing/medical system of the feature-contact position of the target anatomical feature by tagging/registering the exposed face of the target anatomical feature (e.g., papilla face exposed within the target calyx) in some manner. Such tagging may be implemented through provision of user input in some manner or may be substantially automatic based on perceived tissue contact, or the like.

With respect to certain image-based tagging processes, at block 623, the process 600 involves determining the position of the target anatomical feature using image data input and certain neural network functionality, as described in detail below with respect to FIGS. 7 and 8. In some implementations, a convolutional neural network is used for target position identification/tagging.

The feature-contact position recorded in connection with the operation(s) of block 620 may be considered a static position with respect to the potentially dynamic relative position of the target anatomical feature, which may change over time. The feature-contact position may be recorded and/or maintained in any suitable or desirable manner, such as stored in one or more data storage devices.

The process 600 proceeds to subprocesses 630, which may involve tracking the target anatomical feature over an operative period of time while advancing percutaneous-access instrument, such as a needle or the like, in the direction of the target anatomical feature. The real-time tracking of the dynamic relative position of the target anatomical feature can advantageously facilitate accurate direction of the percutaneous-access instrument to the treatment site.

The subprocess 630 may be implemented in various ways. For example, as shown as the subprocess 632, live instrument (e.g., scope) tracking may be implemented to provide operational tracking of the target anatomical feature. For example, throughout the relevant operative period, the distal end of the medical instrument may be maintained in contact with the target anatomical feature (block 634), such that position sensor data indicated by the medical instruments may provide a real-time accurate location of the target anatomical feature. Therefore, as shown at block 636, the live position of the medical instrument may be targeted to provide the desired percutaneous access path. However, with the distal end of the medical instrument in close proximity/contact with the target anatomical feature, real-time visualization of the target anatomical feature may not be possible or sufficiently clear due to the obstruction of the target anatomical feature by the feature itself in the field of view of the camera(s). That is, the camera associated with the local instruments may be sufficiently blocked or obscured by the mass of the target anatomical feature, thereby preventing the physician/user from having visual confirmation of penetration of the target anatomical feature by the percutaneous-access instrument (e.g., needle).

An alternative subprocess 631 is shown for tracking the target anatomical feature while still maintaining a clear visual of the target anatomical feature during approximation of the percutaneous-access instrument. Such subprocess 631 may utilize a static tagged position of the target anatomical feature, as in connection with the operation of block 620. For example, at block 633, the subprocess 631 may involve recording the feature contact position associated with the contact with the target anatomical feature implemented in connection with the operation of block 620, described above.

Rather than continuing to maintain the medical instrument in contact/proximity with the target anatomical feature to provide operational tracking, as with subprocess 632, the subprocess 631 may involve retracting the medical instrument a distance away (e.g., in the proximal direction) from the target anatomical feature to thereby allow the medical instrument to clearly capture the target anatomical feature in a field of view of the camera(s) associated therewith as indicated at block 635. For example, in some implementations, the physician/user may inform the system in some manner when the medical instruments has been parked a desired distance away from the target anatomical feature.

By way of clarification, it is noted that the subprocesses 631, 632 represent alternative implementations of the subprocess 630. That is, the process 600 may generally involve implementation of either the subprocess 632 or the subprocess 631, but not both. For example, the subprocess 632 generally illustrates a solution involving leaving a position-tracking device (e.g., electromagnetic beacon) associated with a wire or scope at the position/surface of the target anatomical feature (e.g., papilla), wherein the position-tracking device can be caused/allowed to move with the papilla during needle insertion. The target position, therefore, can be continuously updated as the sensor moves with the target anatomical feature. The subprocess 632 may generally not require/require any real-time image data. However, the solution of subprocess 632 may not provide immediate visual confirmation of needle puncturing of the target papilla due to obstruction.

In some cases, it may be assumed that the scope remains inside of the target calyx and the papilla-to-scope registration is preserved. In the absence of relative movement of the target anatomical feature with respect to the scope position sensor(s), the target position can be continuously updated based on determined current scope position. For example, the operation(s) associated with block 634 may involve, rather than continually maintaining contact between the instrument/sensor and the target anatomical feature, the scope can be retracted away from the target to allow for camera viewing thereof. The position data (e.g., EM data) collected during retraction of the scope can be used to register/record the papilla location with respect to the scope. For example, according to one use case, the retraction/positioning of the scope could be approximately 5 mm in front of the papilla and 2 mm to the left. Such position offset may be used to determine the position of the target as relative to a current position of the scope. However, relative movement between the target anatomical feature and the scope can result in unreliability of the position offset calculation, and therefore, such processes can be inadequate without compensating for relative movement.

In certain respects, the subprocess 631 may represent an improvement compared to the subprocess 632. For example, reliance on static position data and/or scope-offset data may generally not provide a robust solution in and of itself for compensating for anatomical shift with respect to the target anatomical feature and/or other motion, which may be due to, for example, insertion of the percutaneous-access instrument and/or other factors. In addition to anatomical movement, variance in physical positioning of robotic mechanisms and/or other components associated with the driving/positioning of the medical instrument at the treatment site may further introduce inaccuracies with respect to the relative positioning of the target anatomical feature and the distal end of the medical instrument. With undesired movements of the target anatomical feature, the static recorded position thereof may not be confidently relied upon to provide the actual tracking position of the target anatomical feature. Therefore, it may be desirable for the static target position recorded at block 620 to be updated to accommodate anatomical motion and/or other introduced inaccuracies as described above.

With the medical instrument no longer in contact/proximity with the target anatomical feature, the real-time position of the distal end of the medical instrument may therefore not indicate the real-time position of the target anatomical feature in and of itself. Rather, the subprocess 631 may implement various solutions for tracking location of the target anatomical feature based on the static position recorded/tagged in connection with the operation of block 633. For example, at block 637, the subprocess 631 may involve tracking the location of the target anatomical feature by processing real-time image(s) of the target anatomical feature using neural network circuitry and/or other image-tracking functionality implemented by certain system control circuitry in accordance with embodiments of the present disclosure. For example, the neural network and/or other image-tracking mechanism(s) may receive as input real-time image(s) of the target anatomical feature, wherein the neural network circuitry and/or other image-tracking mechanism(s) is/are configured to identify, and determine a position of, the target anatomical feature therein. Such feature-identification functionality may be used to track the target anatomical feature in real-time relative to the static position recorded in connection with block 633.

The subprocess 631 may or may not include/involve the contacting 624 and retracting 635 steps, wherein the user physically contacts the target papilla location and retracts the scope to show the papilla in the field of view of the scope. For example, where image-based tagging 621 is implemented in connection with block 620, it may not be necessary to physically contact the target anatomical feature to determine the position/location thereof. Rather, the position/location may be determined using target-identification mechanisms disclosed herein based on image data captured/generated by one or more cameras of the scope/instrument. For example, in some embodiments, the target is identified and tracked using multiple frames of image/vision and/or position (e.g., EM) data. Examples of such target position determination are described below in connection with FIG.

12. In some implementations, by looking at the target anatomical feature (e.g., papilla) from two distinct positions and/or alignments, the target position can be estimated/determined with respect to three-dimensional space.

At block 639, the subprocess 631 involves targeting the tracked location of the target anatomical feature with the percutaneous-access instrument. For example, the centroid of an identified papilla shape or form in a real-time image of the treatment site may be used at the target position for a percutaneous-access instrument.

At block 640, the process 600 involves puncturing the target anatomical feature, either without visual confirmation to the target anatomical feature with respect to the subprocess 632 or with visual confirmation in accordance with the subprocess 631, depending on the particular implementation of the process 600.

The various position sensors used in connection with embodiments of the present disclosure, such as for recording the feature-contact position at block 633 or targeting the live instrument position at block 636, may be any type of position sensors. As an example, such sensor(s) may be electromagnetic (EM) sensors/probes. With respect to the scope, the position sensor may be attached or integrated with, proximal to, the tip thereof. Alternatively, the sensor(s) may comprise a coil connected to an electrical wire running the length of the scope, which is connected to external control circuitry configured to interpret electrical signals generated at the coil and passed down the wire. Examples of types of position sensor devices that may be implemented in connection with embodiments of the present disclosure include, but are not limited to, accelerometers, gyroscopes, magnetometers, fiber optic shape sensing (e.g., via Bragg gratings, Rayleigh scattering, interferometry, or related techniques), etc. Depending on the implementation, registration to a separate form of patient imagery, such as a CT scan, may or may not be necessary to provide a frame of reference for locating a urinary stone within the patient.

For reference, certain position determining/localization mechanisms are described that may be implemented in some of the disclosed embodiments. With respect to EM-type sensors, such as coils or other antennas, such sensor devices can be configured detect changes in EM fields as the EM sensor moves within the field (e.g., within the kidney). Therefore, certain embodiments are implemented using one or more EM generators configured to emit EM fields that are picked up by the EM sensor(s). The EM generator(s) may be modulated in any suitable or desirable way, such that when their emitted fields are captured by the EM sensor(s) and are processed by appropriate control circuitry, signals from different EM generators are separable to provide additional dimensions of position information. EM generators may be modulated in time or in frequency, and may use orthogonal modulations so that each signal is fully separable from each other signal despite possibly overlapping in time. Further, separate EM generators may be oriented relative to each other in Cartesian space at non-zero, non-orthogonal angles so that changes in orientation of the EM sensor(s) will result in the EM sensor(s) receiving at least some signal from at least one of the EM generators at any instant in time.

With further reference to the recording of the feature-contact position at block 633 of FIG. 6, EM position data may be registered to an image of the patient captured with a different technique other than EM (or whatever mechanism is used to capture the alignment sensor's data), such as a CT scan, in order to establish a reference frame for the EM data. In addition to the scope, the percutaneous-access needle may include one or more position/alignment sensors, such as an EM sensor. Position/alignment data received from the needle EM sensor may be received and processed similarly to scope position data as describe above. The various processes described herein may be performed wholly or partially manually and/or wholly or partially using robotics.

The processes disclosed herein may be implemented in connection with procedures other than kidney stone removal procedures, such as gallbladder stone removal, lung (pulmonary/transthoracic) tumor biopsy, and others. Generally, any type of percutaneous procedure may be performed by using an endoscope configured to capture image data for feature identification and tracking using neural network processing in accordance with embodiments of the present disclosure. Additional examples include stomach operations, esophagus and lung operations, etc. Further, the objects to be removed do not necessarily need to be urinary stones, they may be any object, such as a foreign body or object created within the human body.

Neural-Network-Based Anatomical Feature Identification and Tracking

Figure 7:
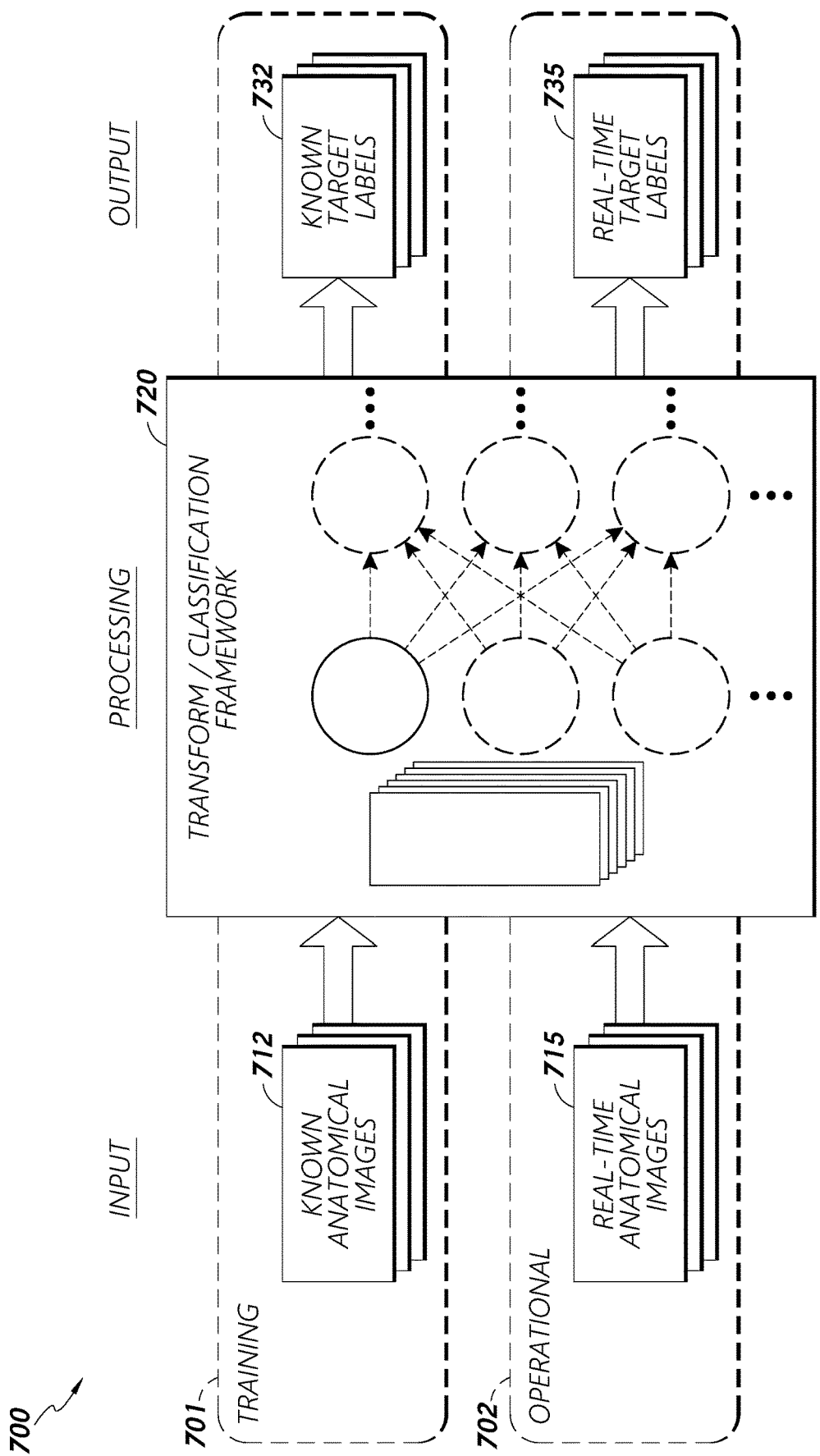
FIG. 7 illustrates a target identification and/or classification architecture in accordance with one or more embodiments.

FIG. 7 illustrates a feature-identification framework for identifying one or more target anatomical features in endoscope camera images for dynamically updating target position data in accordance with one or more embodiments of the present disclosure. The feature-identification framework 700 may be embodied in certain control circuitry, including one or more processors, data storage devices, connectivity features, substrates, passive and/or active hardware circuit devices, chips/dies, and/or the like. For example, the framework 700 may be embodied in the control circuitry 60 shown in FIG. 2 and described above. The feature identification framework 700 may employ machine learning functionality to perform automatic target detection on, for example, ureteroscopic images of internal renal anatomy.

The feature-identification framework 700 may be configured to operate on certain image-type data structures, such as image data representing at least a portion of a treatment site associated with one or more medical procedures. Such input data/data structures may be operated on in some manner by certain transform circuitry 720 associated with an image processing portion of the framework 700. The transform circuitry 720 may comprise any suitable or desirable transform and/or classification architecture, such as any suitable or desirable artificial neural network architecture.

The transform circuitry 720 may be trained according to known anatomical images 712 and target labels 732 corresponding to the respective images 712 as input/output pairs, wherein the transform/classification framework 720 is configured to adjust one or more parameters or weights associated therewith to correlate the known input and output image data. For example, the transform circuitry 720 (e.g., convolutional neural network) may be trained using a labelled dataset and/or machine learning. In some implementations, the machine learning framework may be configured to execute the learning/training in any suitable or desirable manner.

The known target label 732 may be generated at least in part by manually labeling anatomical features in the known anatomical images 712. For example, manual labels may be determined and/or applied by a relevant medical expert to label where, for example, papilla anatomy is among intercalyx anatomical images. The known input/output pairs can indicate the parameters of the transform circuitry 720, which may be dynamically updatable in some embodiments.

The known target label 732 may depict the boundary and/or the internal area of the target anatomical features present therein. In some embodiments, the framework 700 may be configured to generate the real-time target labels 735 in a manner as to indicate in a binary manner whether a particular image of the real-time anatomical images 715 includes a target anatomical feature or not, wherein further processing may be performed on the images that are identified as containing one or more instances of the target anatomical feature to further identify the location and/or other aspects of the target anatomical feature. In some embodiments, further processing may be performed to determine a three-dimensional location of the identified target anatomical feature and/or one or more portions thereof.

The framework 700 may further be configured to generate real-time target label 735 associated with real-time anatomical images 715 using the trained version of the transform circuitry 720. For example, during a medical procedure, real-time images of the treatment site associated with an endoscope or other medical instrument disposed at a treatment site may be processed using the transform circuitry 720 to generate real-time target labels 735 identifying the presence and/or position of one or more target anatomical features in the real-time images. For example, in some implementations, ureteroscope images may be processed by the transform circuitry 720 to identify the presence, position, and/or shape of a target papilla, which may be targeted with a percutaneous-access instrument as described in detail herein. With respect to ureteroscopic applications, papillary anatomy may generally present similarly in appearance across subjects, and therefore papilla anatomy may be identifiable over a broad demographic.

In some embodiments, the transform circuitry 720 may be configured to identify the target anatomical feature(s) (e.g., papilla), as well as segment-out region(s) that contain the identified anatomical feature(s) and/or enclose the identified anatomical feature(s) in the image. The transform framework 720 may comprise an artificial neural network, such as a convolutional neural network. For example, the framework 720 may implement a deep learning architecture that takes in an input image, assigns learnable weights/biases to various aspects/objects in the image to differentiate one from the other. Filters/characteristics of the framework 720 may be hand-engineered or may be learned through machine learning.

The framework 720 may include a plurality of neurons (e.g., layers of neurons, as shown in FIG. 7) corresponding to overlapping regions of an input image that cover the visual area of the input image. The framework 720 may further operate to flatten the input image, or portion(s) thereof, in some manner. The framework 720 may be configured to capture spatial and/or temporal dependencies in the input images 715 through the application of certain filters. Such filters may be executed in various convolution operations to achieve the desired output data. Such convolution operations may be used to extract features, such as edges, contours, and the like. The framework 720 may include any number of convolutional layers, wherein more layers may provide for identification of higher-level features. The framework 720 may further include one or more pooling layers, which may be configured to reduce the spatial size of convolved features, which may be useful for extracting features which are rotational and/or positional invariant, as with certain anatomical features. Once prepared through flattening, pooling, and/or other processes, the image data may be processed by a multi-level perceptron and/or a feed-forward neural network. Furthermore, back-propagation may be applied to each iteration of training. The framework may able to distinguish between dominating and certain low-level features in the input images and classify them using any suitable or desirable technique. In some embodiments, the neural network architecture comprises any of the following known convolutional neural network architectures: LeNet, AlexNet, VGGNet, GoogLeNet, ResNet, or ZFNet.

The input to the framework 720 can be video or still images. In some embodiments, the input comprises video, wherein the framework 720 is configured to produce output that indicates how certain features of the video change over (e.g., implementation of a time model). In some implementations, once the neural network 720 has been trained, operational input to the neural network framework can comprise a plurality (e.g., two) of images, wherein the output 735 comprises data indicating the locations of one or more targets across the images (e.g., over time). The input 715 can comprise images or image data, and/or may comprise data indicating differences between separate (e.g., consecutive) images. For example, the framework 720 can detect motion or spatial change between pixels, wherein a change in pixel position indicates motion between images and/or over time. The output can indicate the difference between images. In some embodiments, the neural network framework 720 is trained to estimate optical flow.

Figure 8:
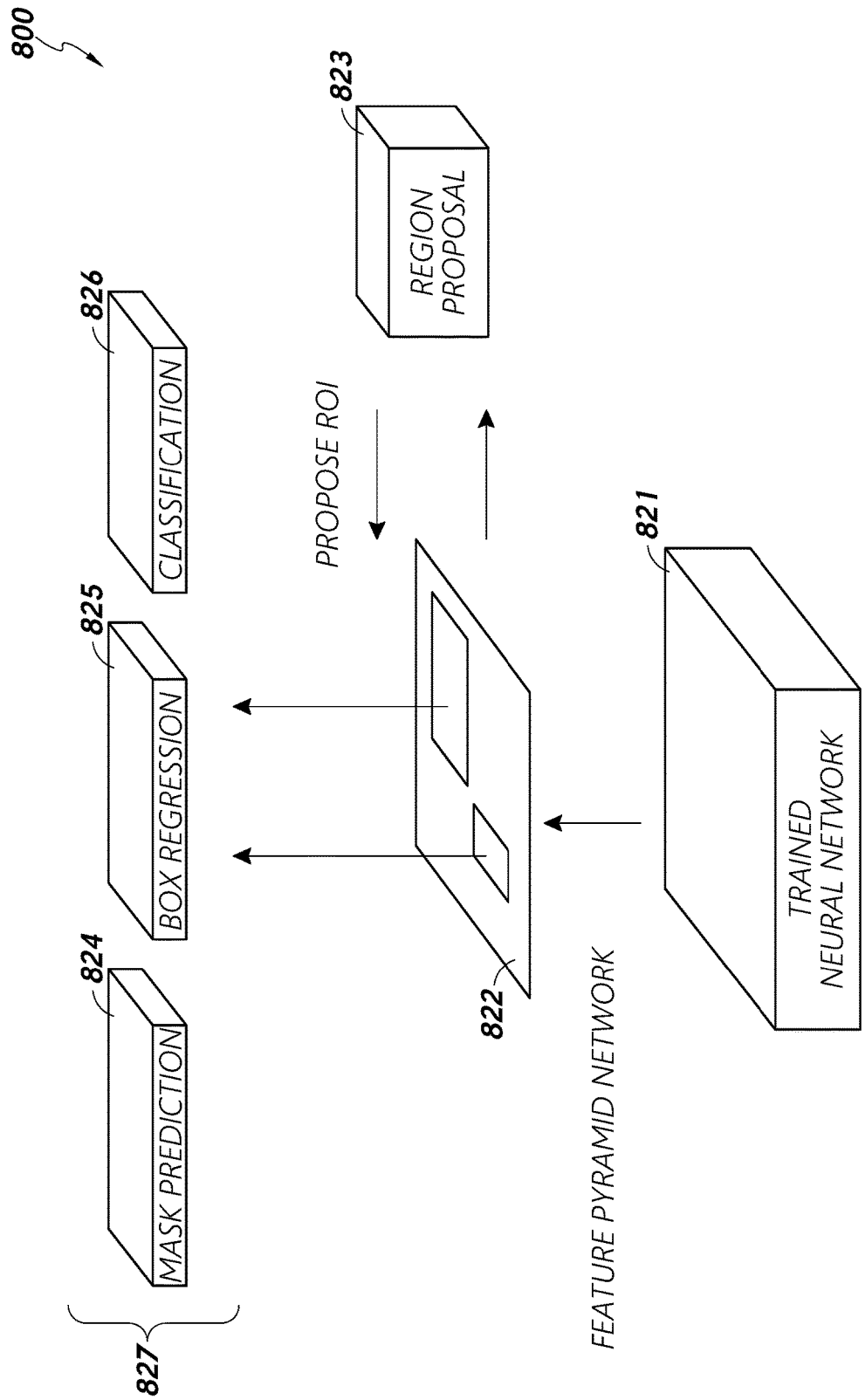
FIG. 8 illustrates a neural-network-based image segmentation architecture in accordance with one or more embodiments.

FIG. 8 illustrates an example neural network feature-classification/identification framework 800 according to one or more embodiments of the present disclosure. The framework 800 may represent a convolutional neural network architecture and may include one or more of the illustrated components, which may represent certain functional components each of which may be embodied in one or more portions or components of control circuitry associated with any of the systems, devices, and/or methods of the present disclosure. The framework 800 may represent an embodiment of the transform circuitry 720 of FIG. 7, or a portion thereof.

The neural network framework 800 may include a pre-trained neural network 821, such as a ResNet 50 neural network, or the like. The framework 800 may further include a feature-extraction component 822 (e.g., feature extraction network (SDN)), such as a feature pyramid network. The feature extraction component 822 may be configured to extract one or more feature maps of an input image and/or engineer feature-detector contours. In embodiments implementing feature pyramid network functionality, multiple images may be processed with different levels of resolution to provide output variants.

The framework 800 may further comprise a region proposal network component 823. The region proposal network 823 may be configured to propose certain bounding boxes on an image that encapsulate targets indicated/identified on feature maps generated and/or provided by the feature extraction component 822.

In some embodiments, a coarse-to-fine processing diagram can be executed to extract the target in an image. Proposed bounding boxes provided by the region proposal network 823 may be used by one or more additional components 827. For example, a binary classification network component 826 may be configured to classify bounding boxes based on whether or not they contain the target feature of interest. Furthermore, a box regression network 825 may be situated and configured to refine boundary boxes proposed by the region proposal network 823. In addition, a mask prediction network component 824 may be configured to calculate and/or represent the silhouette or shape/form of identified target feature(s).

Target Anatomical Feature Tracking

The ability to correctly identify a target anatomical feature, and the position thereof, can advantageously allow for the targeting of the target anatomical feature by a medical instrument during a medical procedure. However, the occurrence of anatomical motion after determination of the target position of the target anatomical feature can cause the target anatomical feature to move away from the known target position. Therefore, embodiments of the present disclosure that provide for the real-time updating of target position data can help obviate issues associated with interoperative anatomical motion.

In some embodiments, a positioning system (e.g., an electromagnetic positioning system as described herein) may be implemented to determine the locations of one or more medical instruments. In some embodiments, the positioning system may be calibrated with camera images to determine the location of features represented in the camera images in the positioning field.

Target anatomical feature tracking can be achieved according to various methodologies. For example, in some embodiments, target tracking can be achieved by comparing the outputs of neural network (or other image processing) circuitry of two consecutively- or sequentially-captured images of the treatment site. For example, given the silhouettes or masks of a target anatomical feature as outputs of a neural network or other type of target-identification circuitry with respect to images captured at different times, the overlap of such silhouettes/masks (e.g., pairwise intersection-over-union (IOU)) such as in the context of percentage of overlap, can be determined. Generally, it may be assumed that the content differences between consecutive images, at least with respect to image capture at a high enough sample rate, do not differ significantly. Therefore, masks of consecutively-captured images can be considered to represent the same target anatomical feature if there overlap percentage is higher than a predefined/predetermined threshold, where the thresholds relates to the maximum movement of targets over the sampling.

Figure 9:
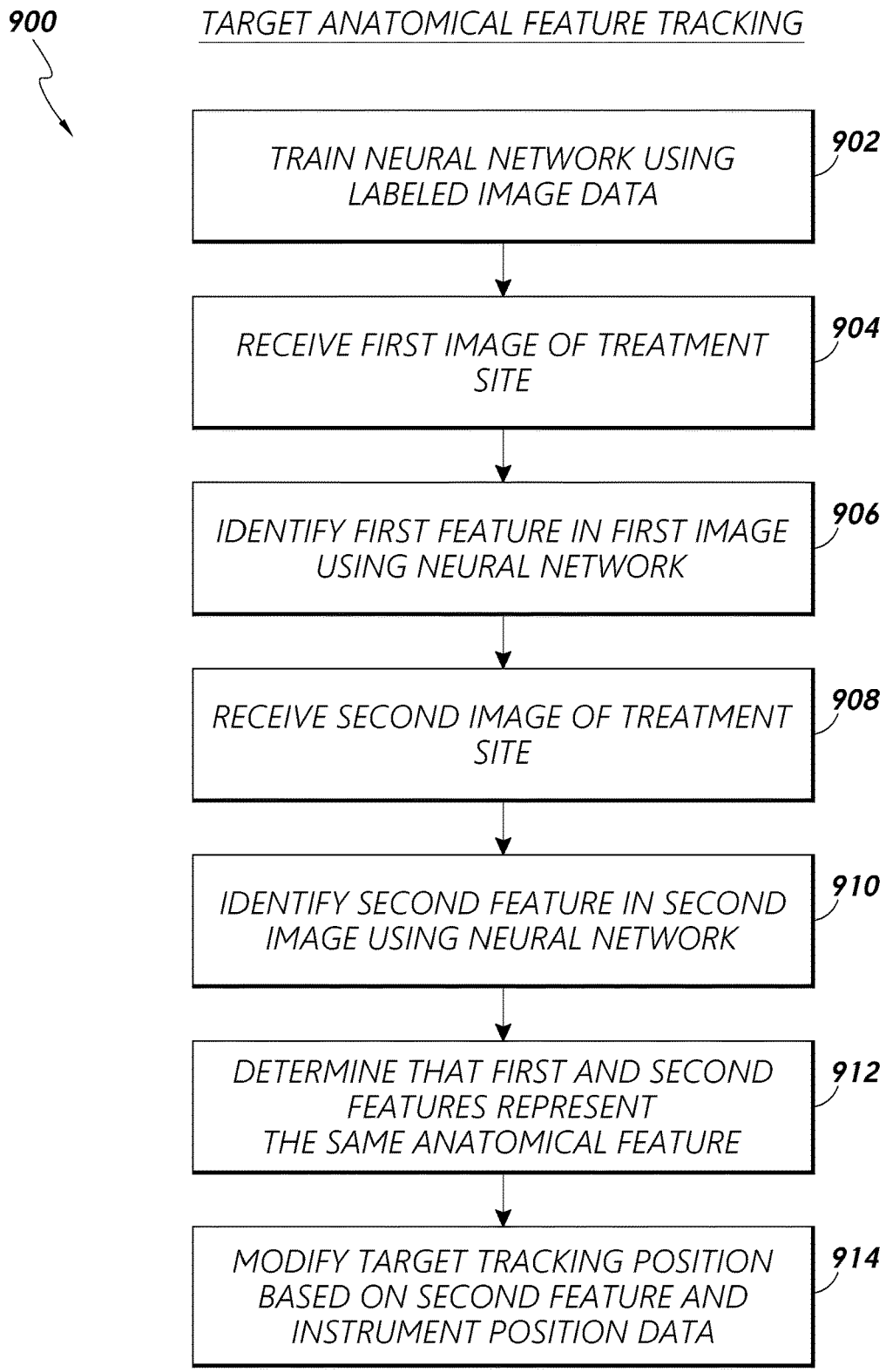
FIG. 9 is a flow diagram illustrating a process for tracking a target anatomical feature in accordance with one or more embodiments.

FIG. 9 is a flow diagram illustrating a process 900 for tracking a target anatomical feature at a treatment site according to one or more embodiments of the present disclosure. At block 902, the process 900 involves training a neural network using labeled image data. For example, the neural network may comprise a framework similar in certain respects to the frameworks 700, 800 shown in FIGS. 7 and 8, respectively.

At block 904, the process 900 involves receiving a first image of the treatment site from an endoscope or other medical instrument disposed at or near the treatment site. At block 906, the process 900 involves identifying a first feature in the first image using a neural network architecture/framework. For example, the first feature may be a target papilla present at the treatment site. For example, one or more machine learning components or modules may be implemented to perform segmentation of the first feature with respect to the first image.

At block 908, the process 900 involves receiving a second image of the treatment site. The second image may be captured consecutively and/or sequentially with respect to the first image. At block 910, the process 900 involves identifying a second feature in the second image using the neural network. For example, the second feature may be a papilla in a target calyx treatment site. At block 912, the process 900 involves determining that the first and second features represent the same target anatomical feature, such as the same target papilla, at the treatment site. The determination that the first and second features represent the same target anatomical feature may be made in any way, such as by comparing determined overlap or movement of the first and second features and/or portion(s) thereof.

At block 914, the process 900 involves modifying a target tracking position associated with the target anatomical feature based on the identified second feature and/or instrument position data. For example, the instrument position data may correspond to an initial tagged position of the medical instrument and/or an articulation or relative movement thereof. Modification of the target tracking position may serve to track the target anatomical feature by compensating for dynamic relative movement thereof. Furthermore, an endoscope or other medical instrument used to capture the first image and the second image may have an electromagnetic sensor or other position sensor associated therewith. Such position sensor may be used to introduce compensation for movement of the medical instrument to the target tracking position data.

Modification of the target tracking position may be necessitated and/or desirable based on relative motion of the target anatomical feature between the time of capture of the first image and the time of capture of the second image. As described above, such motion may be caused by the insertion and/or manipulation of a percutaneous-access instrument, such as a needle, in the general area of the treatment site. Because of the motion, the target anatomical feature (e.g., papilla) may generally not stay fixed with respect to the scope, which may be used to determine the initial target position. Therefore, feature identification and tracking functionality disclosed in connection with systems, devices, and methods of the present disclosure may allow for tracking of the target anatomical feature over time using camera images. Such tracking may be used to predict the three-dimensional location of the target anatomical feature dynamically, wherein the three-dimensional location may be used as the target tracking position for a percutaneous-access instrument, as described herein. Achieving rendezvous between the percutaneous-access instrument and the target anatomical feature may be greatly aided by the dynamic target estimation, as described herein.

The position of the camera of the medical instrument (e.g., endoscope) may be determined in relation to the position of the position sensor associated with the distal end of medical instrument. With such camera position information, the location of an object/feature appearing in image space may be determined with respect to the position space associated with the position sensor (e.g., electromagnetic field space). Therefore, the position of the second feature in the second image may be determined in three-dimensional space and can be provided for direction of the percutaneous-access instrument (e.g., needle).

Although FIG. 9 describes modifying the target tracking position based on the second feature identification and/or position, it should be understood that any type of responsive action may be implemented based at least in part on updated anatomical feature identification. For example, certain control circuitry communicatively coupled to robotics controlling the position of the endoscope may be implemented to thereby adjust/articulate the scope based on the movement of the target anatomical feature. For example, the scope can be moved such that a centroid or other portion of the target anatomical feature is positions at or near a center of a field of view of a camera, interface, or other visual representation of the treatment site.

Neural network and masking concepts disclosed herein can be implemented in accordance with aspects of the publication "Mask R-CNN," (He, Kaiming, Georgia Gkioxari, Piotr Dollar, and Ross Girshick. "Mask r-cnn." In Computer Vision (ICCV), 2017 IEEE International Conference on, pp. 2980-2988. IEEE, 2017), the entire contents of which are hereby expressly incorporated by reference.

Figures 2, 10:
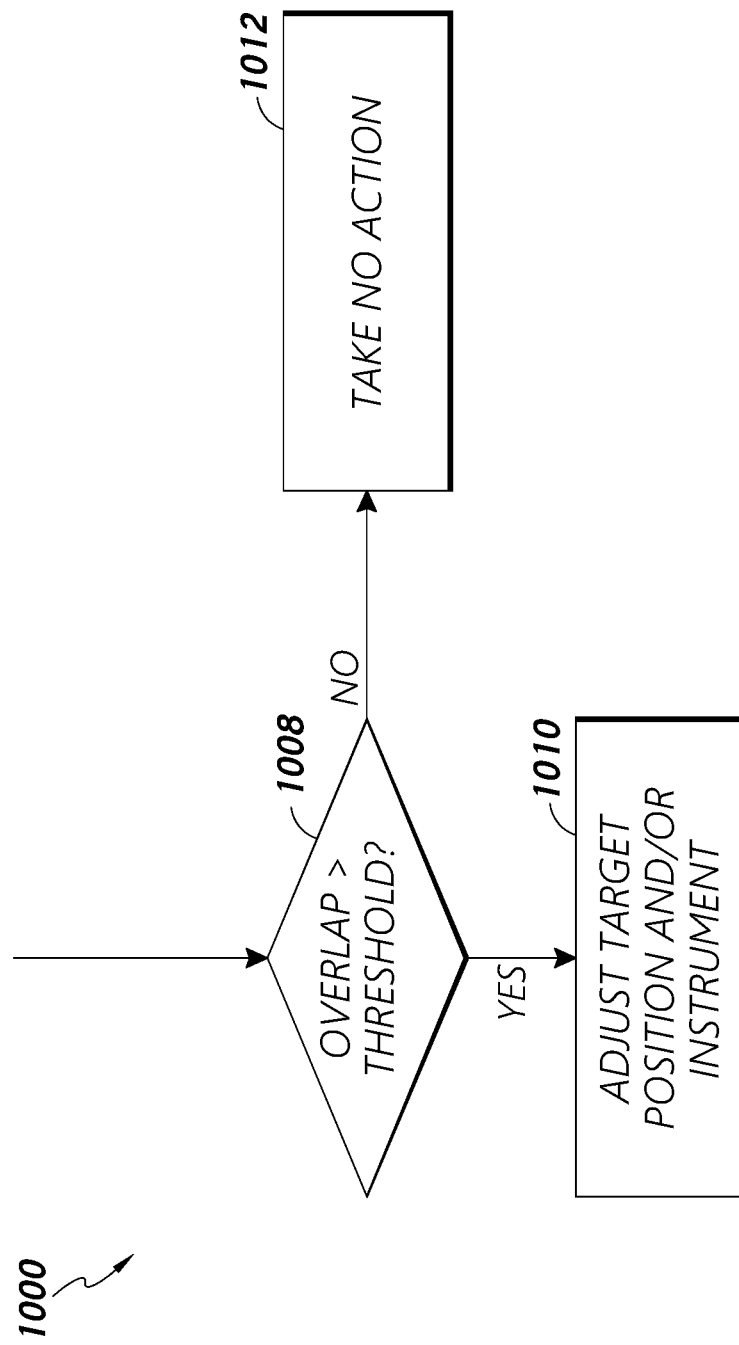

FIG. 10 is a flow diagram illustrating a process for tracking a target anatomical feature at a treatment site in accordance with one or more embodiments of the present disclosure. The tracking process 1000 of FIG. 10 may be considered a direct tracking embodiment. FIG. 11 shows certain feature mask and related images relating to the various steps of the process 1000 shown in FIG. 10.

At block 1002, the process 1000 involves generating a target mask 122 for a first image 121 of the treatment site taken at a first time (t). As shown in the image 121, the first image includes at least a portion of a target anatomical feature 111, which may represent a papilla visible from within a calyx/kidney treatment site. The image 122 represents a mask of the target anatomical feature. Although any mask may be used in accordance with embodiments of the present disclosure, the illustrated mask 122 is a binary mask including a feature area 112 representing a shape or form of the visible portion of the target anatomical feature 111, and a background portion 119 representing the area of the image 121 that does not correspond to the target anatomical feature 111. The mask 122 may be generated using any type of segmentation and/or machine learning mechanism, with the segmented regions bifurcated to provide a region mask, as shown.

At block 1004, the process 1000 involves generating a target mask 124 for a second image 123 taken the time (t+1) that is subsequent to the time (t) when the first image 121 was captured. Through neural network image processing, or other target-identification mechanism in accordance with aspects of the present disclosure, the target anatomical feature 113 may be identified in the image 123. The mask 124 of the image 123 with respect to the target feature 113 is shown as the image 124, which includes a feature area 114 representing a shape/silhouette or form of the visible portion of the target anatomical feature 113 and the image 123 and a background portion 127 representing the area of the image 123 that does not correspond to the target anatomical feature 113.

At block 1006, the process 1000 involves determining target or feature overlap in the first 121 and second 123 images using the respective masks 122, 124 thereof. The image 125 represents an overlay of the first mask 122 and the second mask 124. The resulting image 125 includes a portion 115 that corresponds to background for both the first image 121 and the second image 123, a portion 116, which corresponds to background with respect to the first image 121 but feature area with respect to the second image 123, and a portion 117, which corresponds to background with respect to the second image 123 but feature area with respect to the first image 121. The remaining area 118 represents an area of overlap between the identified anatomical features 111, 113. The overlap area/shape is shown separately as image 126 for clarity and represents an area not greater than either of the feature areas of the masks 122, 124.

The process 1000 may proceed to decision block 1008, where it may be determined whether the amount of overlap 118, 126 is greater than a predetermined threshold amount of overlap with respect to the area of the first feature area 112, the second feature area 114, or both. If the determination is in the affirmative, the process 1000 proceeds to block 1010, wherein a responsive action may be taken. For example, at block 1010, it may be assumed that the first identified anatomical feature 111 and the second identified anatomical feature 113 represent the same target anatomical feature. For example, both identified features may represent the same papilla within the kidney of a patient. Therefore, any change in position between the images 121 and 123 may represent anatomical movement, and therefore responsive action may involve adjusting a target position associated with the target anatomical feature and/or adjusting a position of a medical instrument being utilized, such as the instrument utilized to capture the images 121, 123 (e.g., an endoscope and/or camera thereof). For example, one or more robotic arms may be configured to respond by adjusting the arm(s) and/or an endoscope position controlled by the robotic arm(s). Determination of overlap of the relevant regions may be based on two-dimensional X/Y axes. Although the difference between the images 121, 123 is described as being attributed to the anatomical movement, it should be understood that such differences may be attributable at least in part to movements of one or more operational tools or instruments.

If the feature overlap does not meet the predetermined threshold, the process 1000 may proceed to block 1012, which may or may not be associated with any responsive action. For example, at block 1012, it may be assumed that the features 111, 113 represent separate anatomical features and/or portions thereof. Therefore, the differences in position between the features 111, 113 may not be relied upon as representing particular anatomical movement of a target anatomical feature. In some embodiments, the predetermined threshold may be dynamically tunable, and may be selected and/or determined to produce desirable or optimal differentiating performance. For example, the threshold may be determined based on analysis of prior known data, as described herein. In some embodiments, movements that can be attributed to cyclical respiratory action may be filtered out, such that such movement is not attributed to movements of the target anatomical feature. For example, the sampling of the images 121, 123 may be performed such that they correspond to similar points in the period of the respiratory cycle. In some implementations, the images are sampled at approximately 30 frames per second, or any other suitable or desirable sampling rate.

In addition to direct tracking methods as described above, indirect tracking methods may be implemented in accordance with the present disclosure. For example, optical flow tracking may be implemented in order to track the movements of target anatomical feature portions and/or corresponding pixel representations thereof across multiple images. For example, tracking pixels representative of a common image feature may provide target anatomical feature movement information. Furthermore, other feature-tracking mechanisms may be implemented, such as tracking of corners, blogs, pixel groups, and/or any other image features.

Although segmentation/masking can be performed using image processing methodologies as described herein, including neural network frameworks and the like, in some implementations, segmentation/masking is performed at least partially manually by the physician or other technician/operator. For example, the technician may select the target anatomical feature and identify similar features in subsequent image(s), wherein the movement represented by the sequential feature identification/segmentation can be accounted for in any suitable or desirable manner in accordance with presents disclosure. In some implementations, feature descriptors may be run locally in the identified feature area, which may be considered an area in which there is a high likelihood of feature presence in subsequent images.

Although aspects of the present inventive disclosure are presented in the context of ureteroscope, it should be understood that such concepts are applicable to any type of endoscopy application. For example, the feature identification and tracking techniques described herein may be utilized for the purpose of identifying and tracking polyps or other target anatomical features. With respect to bronchoscopy procedures, target anatomical feature identification and tracking concepts of the present disclosure may be utilized to identify tumors and/or manage scope position for the purpose of collecting samples or the like. With respect to respiratory procedures, feature identification and targeting in accordance with the present disclosure may be utilized to identify and/or track nodules inside the target airway, airways themselves, and/or other features.

With respect to any of the embodiments disclosed herein, it should be understood that known scope movement data may be compensated for with respect to target anatomical feature identification and/or tracking. Furthermore, position sensor information may further provide information indicating movement for which compensation may be made for target feature tracking purposes. With further reference to FIG. 10, in some embodiments, before initiating any responsive action at block 1010, the process 1000 may involve determining whether user-initiated scope movement or unintentional scope movement has taken place. If so, a generated mask may be adjusted to compensate for such movement such that such movement is not reflected in the overlap determination and/or responsive actions.

With respect to the various embodiments disclosed herein, position information may be determined and/or generated using any suitable or desirable type of sensor, device, or combination thereof. For example, position sensors/devices of the present disclosure may include one or more of any of the following: electromagnetic sensors, impedance spectroscopy sensors, coaxial sensors, inertial measurement sensors, accelerometers, magnetic meters, gyroscopes, and/or any other type of sensor providing information indicating a position, distance, orientation, acceleration, alignment, or the like.

Three-Dimensional Target Position Estimation

Three-dimensional (3D) position estimation for the purpose of target anatomical feature tracking in accordance with aspects of the present disclosure may be implemented according to any suitable or desirable technique or mechanism. For example, in some embodiments, distance between an endoscope camera and a target anatomical feature may be estimated based on the representative size of the anatomical feature in an image.

In some embodiments, information relating to angle of movement of a scope and/or anatomical feature may be used to determine 3D position. For example, electromagnetic sensors/beacons in an electromagnetic field/space can provide such angle of movement information. By combining electromagnetic sensor data with image data, mappings between distance from the target anatomical feature and size of the target anatomical feature in a resulting image captured after the movement of such distance can be used to estimate depth/distance of features in subsequent images. In some embodiments, when contacting the target anatomical feature (e.g., a papilla) and retracting the scope away from such feature to park the scope in a position to provide a desirable field of view, the distance traveled may be registered using, for example, electromagnetic sensor data. Furthermore, subsequent images and provide information relating to how large the anatomical feature appears in such images, and therefore the relationship/mapping between feature size and distance can be determined and used for future position determination. In some implementations, machine learning may be utilized to classify images and determine position information based on the size of features in such images.

In some embodiments, machine learning may be utilized to train a neural network framework to interpret image data and produce output indicating 3D depth of image pixels. Such machine learning may be implemented according to any suitable or desirable process or mechanism described herein. In some embodiments, external camera sensor(s) associated with medical instruments (e.g., scopes) can be utilized to obtain the 3D location of the target. For example, structured-lighting sensor(s) and/or time-of-flight sensor(s) can be used in determination of 3D positioning.

According to some embodiments, a geometric translation approach may be implemented to detect the 3D position of a target anatomical feature. For example, as with certain other embodiments of the present disclosure, potential images may be captured that are associated with separate timestamps. In connection with such images, rotational translation information with respect to the camera, which may be determined based on sensor information from any suitable or desirable sensor or device, may be used to triangulate and/or determine the positions of such images in 3D space, thereby providing information indicating 3D location of target anatomical feature(s) in the 3D space. The rotational translation information may be based on robotic actuator movement and/or position sensor information, such as from an electromagnetic beacon device associated with the camera and/or scope and indicating a position of the camera in the electromagnetic field space.

Figure 12:
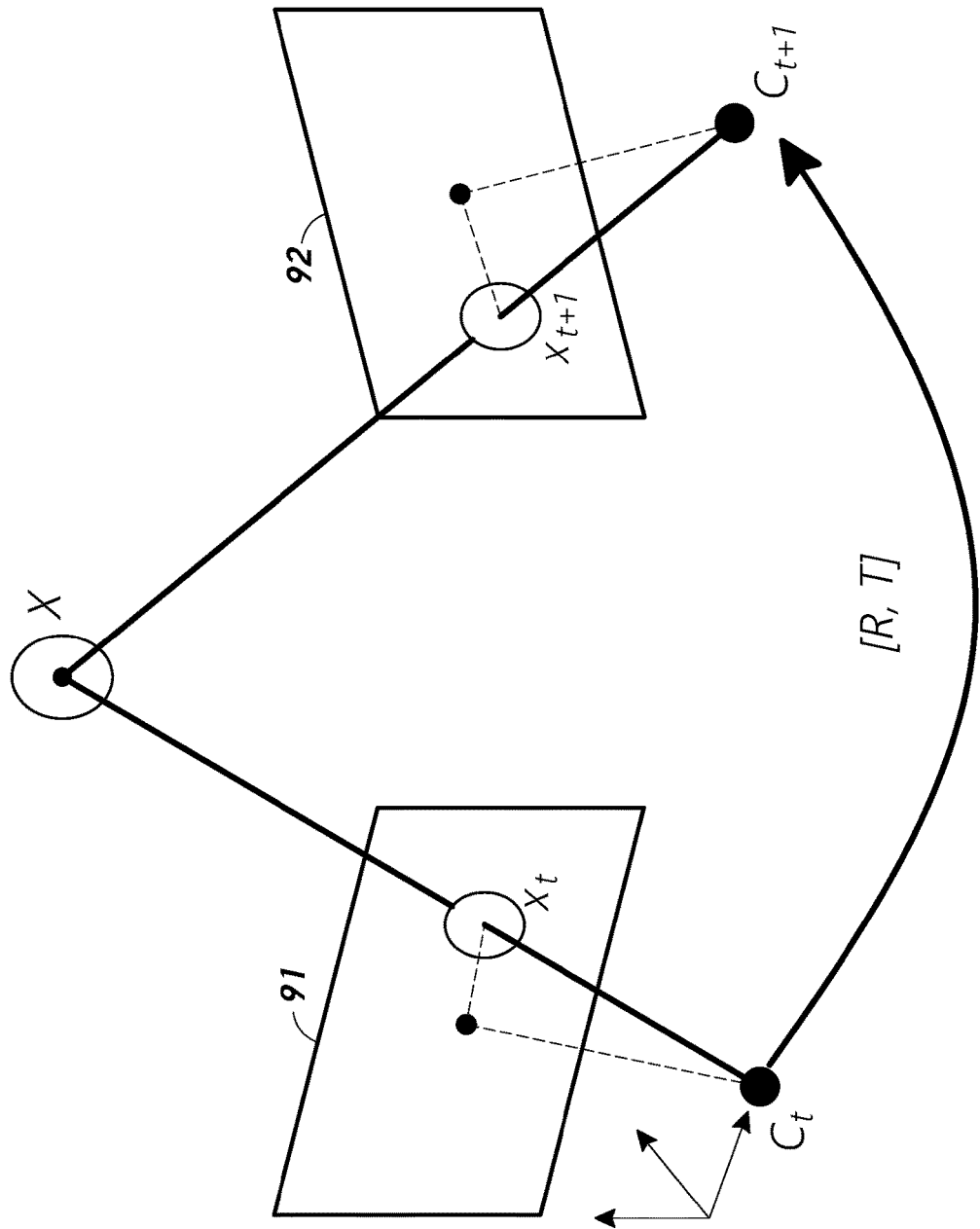
FIG. 12 illustrates a three-dimensional position estimation framework according to one or more embodiments.

FIG. 12 is a diagram illustrating aspects of a 3D position estimation process involving first 91 and second 92 images taken at separate times, namely times corresponding to time (t) and time (t+1), respectively (referred to as $C_t$ and $C_{t+1}$).

Given the intrinsic and extrinsic parameters (principle points, focal length and distortion factors, relative motion) of the camera, we can then calculate the 3D location of the target anatomical feature based at least in part on the tracked target two-dimensional (2D) locations on the images. For intrinsic parameters, the camera principle point and focal length may be accounted for. Additional data that may be taken into account may include radial and tangential distortion factors. Based on the sensor readings (e.g., either robotic- or EM-based), extrinsic parameters may also be obtained, including rotation R and translation T of the scope between the locations where the two images were taken. For convenience, K may be denoted as a matrix that contains the intrinsic parameters and H denoted as a 4-by-4 matrix that contains the extrinsic rotation and translation between $C_t$ and $C_{t+1}$.

For $C_t$, the 3D-to-2D projection relationship can be expressed as $x_t = KX$, where X is the 3D coordinate w.r.t. $C_t$ and $x_t$ is the 2D coordinate (detected centroid of a target) on image t. Here, K is a three-by-4 matrix that can be expressed as:

$$K = \begin{bmatrix} K_{(1)} \\ K_{(2)} \\ K_{(3)} \end{bmatrix},$$

with $K_{(n)}$ being the n-th row in K.

Similarly, for $C_{t+1}$, $x_{t+1}=K'X$, where:

$$K' = KH = \begin{bmatrix} K'_{(1)} \\ K'_{(2)} \\ K'_{(3)} \end{bmatrix}.$$

As $x_t$ and KX are parallel vectors, $x_t \times KX=0$, and similarly, $x_{t+1} \times K'X=0$. Here, 'x' is the cross-product operator. Hence:

$$x_t \times KX = 0 \Rightarrow \det \begin{bmatrix} i & j & k \\ u_t & v_t & 1 \\ K_{(1)}X & K_{(2)}X & K_{(3)}X \end{bmatrix} = 0,$$

The above may produce: $i(v_t K_{(3)}X - K_{(2)}X) - j(u_t K_{(3)}X - K_{(1)}X) + k(u_t K_{(2)}X - v_t K_{(1)}X) = 0$, where $u_t$ and $v_t$ are the 2D coordinates of $x_t$. Hence:

$v_t K_{(3)}X - K_{(2)}X = 0$ $u_t K_{(3)}X - K_{(1)}X = 0$ $u_t K_{(2)}X - v_t K_{(1)}X = 0$

Here, only the first two equations may be needed, as the third equation is a linear combination of the first two. Similarly, for $C_{t+1}$, the following two equations can be obtained:

$v_{t+1} K'_{(3)}X - K'_{(2)}X = 0$ $u_{t+1} K'_{(3)}X - K'_{(1)}X = 0$

After stacking the equations of $C_t$ and $C_{t+1}$, the following may be produced:

$AX=0$, where A is 4-by-4 matrix:

$$A = \begin{bmatrix} v_t K_{(3)} - K_{(2)} \\ u_t K_{(3)} - K_{(1)} \\ v_{t+1} K'_{(3)} - K'_{(2)} \\ u_{t+1} K'_{(3)} - K'_{(1)} \end{bmatrix}.$$

As the elements in A are known (detected 2D coordinates, intrinsic and extrinsic parameters), X can be calculated by performing singular value decomposition (SVD) on A:

$A = U\Sigma V^T$, and the last column of V is the solution of X.

Therefore, in view of the foregoing disclosure, the various inventive concepts disclosed herein may be utilized to perform automatic target detection, target tracking, and/or three-dimensional position estimation. In some embodiments, aspects of the present disclosure advantageously allow for target anatomical feature tracking without requiring physical contact with the target anatomical feature, which may facilitate improved ergonomics of the usage of the ureteroscope.

Control circuitry configured to implement the system of FIG. 12 can advantageously generate three-dimensional (3D) location information associated with a target present in two (e.g., temporally consecutive) images. In some implementations, the 3D information can be generated using a neural network framework, which may be similar in one or more respects to the framework 720 shown in FIG. 7 and described above as an alternative, or in addition, to the computational implementation described above. For example, the input(s) to the neural network can comprise images, labels or other data indicating 3D size of target anatomy, 3D location (e.g., xyz coordinates), or other data relating to image parameters. Depth information can be determined from CT, or can be derived from other information. For example, depth and/or pixel coordinate information can be output(s) from the neural network.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A method of tracking an anatomical feature, the method comprising:
    advancing an instrument to an operational environment including a target anatomical feature of a subject, the instrument comprising an imaging device;
    generating a first image of a first portion of the operational environment using the imaging device of the instrument when the instrument is in a first position;
    identifying a first representation of the target anatomical feature in the first image;
    generating a second image of a second portion of the operational environment using the imaging device of the instrument when the instrument is in a second position;
    identifying a second representation of the target anatomical feature in the second image;
    determining a first set of parameters associated with the instrument in the first position;
    determining a second set of parameters associated with the instrument in the second position; and
    generating a three-dimensional position of the target anatomical feature based at least in part on the first representation of the target anatomical feature in the first image, the second representation of the target anatomical feature in the second image, the first set of parameters, and the second set of parameters.

2. The method of claim 1, wherein the first set of parameters and the second set of parameters comprise electromagnetic sensor data.

3. The method of claim 1, wherein at least one of the first set of parameters or the second set of parameters indicates rotational translation of the instrument between the first position and the second position.

4. The method of claim 1, wherein generating the three-dimensional position is based on sensor position data of the first set of parameters and the second set of parameters.

5. The method of claim 1, wherein each of the first set of parameters and the second set of parameters comprises one or more of the following parameters: focal length, distortion, or relative motion.

6. The method of claim 1, wherein the first set of parameters includes both intrinsic and extrinsic parameters, wherein the intrinsic parameters are indicative of one or more internal properties of the imaging device, and wherein the extrinsic parameters are indicative of one or more positional properties of the imaging device with respect to the operational environment.

7. The method of claim 1, wherein the first representation is indicative of a size of the target anatomical feature, and the method further comprising:
    estimating a distance between the instrument and the target anatomical feature when the instrument is in the first position based on the size of the target anatomical feature.

8. The method of claim 7, wherein the first set of parameters comprises the distance.

9. The method of claim 7, further comprising determining a mapping between the size of the target anatomical feature and the estimated distance.

10. The method of claim 9, wherein estimating the distance between the instrument and the target anatomical feature is based on the mapping.

11. A system for tracking an anatomical feature, the system comprising:
    an instrument comprising an imaging device; and
    control circuitry communicatively coupled to the instrument, wherein the control circuitry is configured to cause the system to perform operations comprising:
        advancing the instrument to an operational environment including a target anatomical feature of a subject;
        generating a first image of a first portion of the operational environment using the imaging device of the instrument when the instrument is in a first position;
        identifying a first representation of the target anatomical feature in the first image;
        generating a second image of a second portion of the operational environment using the imaging device of the instrument when the instrument is in a second position;
        identifying a second representation of the target anatomical feature in the second image;
        determining a first set of parameters associated with the instrument in the first position;
        determining a second set of parameters associated with the instrument in the second position; and
        generating a three-dimensional position of the target anatomical feature based at least in part on the first representation of the target anatomical feature in the first image, the second representation of the target anatomical feature in the second image, the first set of parameters, and the second set of parameters.

12. The system of claim 11, wherein the instrument further comprises an electromagnetic position sensor, wherein the first set of parameters and the second set of parameters comprise electromagnetic sensor data.

13. The system of claim 11, wherein at least one of the first set of parameters or the second set of parameters indicates rotational translation of the instrument between the first position and the second position.

14. The system of claim 11, wherein generating the three-dimensional position is based on sensor position data of the first set of parameters and the second set of parameters.

15. The system of claim 11, wherein each of the first set of parameters and the second set of parameters comprises one or more of the following parameters:

focal length, distortion, or relative motion.

16. The system of claim 11, wherein the first set of parameters includes both intrinsic and extrinsic parameters, wherein the intrinsic parameters are indicative of one or more internal properties of the imaging device, and wherein the extrinsic parameters are indicative of one or more positional properties of the imaging device with respect to the operational environment.

17. The system of claim 11, wherein the first representation is indicative of a size of the target anatomical feature, and wherein the operations further comprise;

estimating a distance between the instrument and the target anatomical feature when the instrument is in the first position based on the size of the target anatomical feature.

18. The system of claim 17, wherein the first set of parameters comprises the distance.

19. The system of claim 17, wherein the operations further comprise determining a mapping between the size of the target anatomical feature and the estimated distance.

20. The system of claim 19, wherein estimating the distance between the instrument and the target anatomical feature is based on the mapping.

* * * * *